US012588801B2

(12) United States Patent
Hacker et al.

(10) Patent No.: US 12,588,801 B2
(45) Date of Patent: Mar. 31, 2026

(54) PORT CONNECTORS

(71) Applicant: IDEATE Medical, Inc., St. Louis, MO (US)

(72) Inventors: Tom Hacker, Hood River, OR (US); Philippe Conseil, Montaigu-Vendee (FR); William Wong, Encinitas, CA (US); Florencia Chicatun, Saint-Laurent (CA)

(73) Assignee: IDEATE Medical, Inc., St. Louis, MO (US)

( * ) Notice: Subject to any disclaimer, the term of this patent is extended or adjusted under 35 U.S.C. 154(b) by 908 days.

(21) Appl. No.: 17/824,059

(22) Filed: May 25, 2022

(65) Prior Publication Data

US 2022/0378281 A1 Dec. 1, 2022

Related U.S. Application Data

(60) Provisional application No. 63/193,377, filed on May 26, 2021.

(51) Int. Cl.
*A61B 1/00* (2006.01)
*A61L 2/16* (2006.01)
*G02B 23/24* (2006.01)
(52) U.S. Cl.
CPC ............ *A61B 1/00128* (2013.01); *A61L 2/16* (2013.01); *G02B 23/2476* (2013.01)
(58) Field of Classification Search
CPC . A61B 1/00128; A61B 1/00131; A61B 1/125; A61L 2/16; A61L 2/26;

(Continued)

(56) References Cited

U.S. PATENT DOCUMENTS 4,405,312 A 9/1983 Gross et al.
4,410,492 A 10/1983 Kay
(Continued)

FOREIGN PATENT DOCUMENTS

EP 0345713 A1 12/1989
EP 2283789 A1 2/2011
(Continued)

OTHER PUBLICATIONS

Japanese Notification of Reason(s) for Refusal received for Japanese Patent Application Serial No. 2023-573065 dated Oct. 8, 2024, 12 pages (Including English Translation).
(Continued)

*Primary Examiner* — Kathryn Elizabeth Limbaugh
(74) *Attorney, Agent, or Firm* — Stinson LLP

(57) ABSTRACT

The present disclosure relates to port connectors for sterilizing the exposed surfaces of a fluid port of an article to be sterilized to a sterilization apparatus. The port connector can include a housing that couples to the fluid port. The housing may define an inlet that fluidly couples to the fluid port, an outlet that fluidly couples to the sterilization apparatus, and a fluid passageway fluidly coupling the inlet and outlet. The port connector can include a porous member supported by the housing. The porous member has a porous structure defining a plurality of minute passageways. The porous member is arranged relative to the housing to engage the fluid port when the port connector is connected to the fluid port.

21 Claims, 19 Drawing Sheets

(58) Field of Classification Search
CPC .......... A61L 2202/123; A61L 2202/15; A61L
2202/24; G02B 23/2476; A61M 39/1011;
A61M 39/16
See application file for complete search history.

(56) References Cited

U.S. PATENT DOCUMENTS

| | | | |
|---|---|---|---|
| 4,943,414 | A | 7/1990 | Jacobs et al. |
| 5,266,275 | A | 11/1993 | Faddis |
| 5,288,467 | A | 2/1994 | Biermaier |
| 5,356,396 | A | 10/1994 | Wyatt et al. |
| 5,492,672 | A | 2/1996 | Childers et al. |
| 5,527,508 | A | 6/1996 | Childers et al. |
| 5,552,115 | A | 9/1996 | Malchesky |
| 5,667,753 | A | 9/1997 | Jacobs et al. |
| 5,733,503 | A | 3/1998 | Kowatsch et al. |
| 5,792,422 | A | 8/1998 | Lin et al. |
| 5,869,000 | A | 2/1999 | Decato |
| 6,013,227 | A | 1/2000 | Lin et al. |
| 6,036,918 | A | 3/2000 | Kowanko |
| 6,041,794 | A | 3/2000 | Lin et al. |
| 6,187,266 | B1 | 2/2001 | Lin et al. |
| 6,312,646 | B2 | 11/2001 | Kowanko |
| 6,365,103 | B1 | 4/2002 | Fournier |
| 6,660,227 | B2 | 12/2003 | Ordaz |
| 6,835,362 | B1 | 12/2004 | Eriksson |
| 6,841,124 | B2 | 1/2005 | Chien et al. |
| 6,939,519 | B2 | 9/2005 | Agamohamadi et al. |
| 6,986,736 | B2 | 1/2006 | Williams et al. |
| 7,252,800 | B2 | 8/2007 | Jacobs et al. |
| 7,267,806 | B2 | 9/2007 | Kendall et al. |
| 7,300,638 | B2 | 11/2007 | Williams et al. |
| 7,452,504 | B2 | 11/2008 | Wu et al. |
| 7,608,218 | B2 | 10/2009 | Fryer et al. |
| 7,744,832 | B2 | 6/2010 | Horacek et al. |
| 7,803,316 | B2 | 9/2010 | Lin et al. |
| 7,922,701 | B2 | 4/2011 | Buchman |
| 8,182,759 | B2 | 5/2012 | Kuroshima |
| 8,506,900 | B1 | 8/2013 | Ricciardi et al. |
| 8,641,684 | B2 | 2/2014 | Utterberg et al. |
| 8,663,555 | B2 | 3/2014 | Shiosawa |
| 8,840,836 | B2 | 9/2014 | Olson |
| 9,017,607 | B2 | 4/2015 | Olson et al. |
| 9,173,602 | B2 | 11/2015 | Gilbert |
| 10,582,984 | B2 | 3/2020 | Nguyen et al. |
| 11,795,044 | B2 | 10/2023 | Nguyen et al. |
| 12,161,771 | B2 | 12/2024 | Conseil et al. |
| 2003/0063997 | A1 | 4/2003 | Fryer et al. |
| 2004/0017382 | A1 | 1/2004 | Butcher |
| 2004/0017824 | A1 | 1/2004 | Koenck et al. |
| 2004/0091389 | A1 | 5/2004 | Malkin et al. |
| 2005/0000553 | A1 | 1/2005 | Noguchi et al. |
| 2005/0025685 | A1 | 2/2005 | Selig |
| 2007/0048177 | A1 | 3/2007 | Szu-Min et al. |
| 2009/0286030 | A1 | 11/2009 | Robert et al. |
| 2010/0004510 | A1 | 1/2010 | Kuroshima |
| 2010/0040521 | A1 | 2/2010 | Horacek et al. |
| 2011/0064512 | A1 | 3/2011 | Shaw et al. |
| 2011/0176959 | A1 | 7/2011 | Suek |
| 2011/0232700 | A1 | 9/2011 | Suzuki et al. |
| 2012/0007352 | A1 | 1/2012 | Nguyen et al. |
| 2013/0171030 | A1 | 7/2013 | Ferlic et al. |
| 2015/0336139 | A1 | 11/2015 | Deprey et al. |
| 2016/0297152 | A1 | 10/2016 | Maggiore |
| 2016/0324997 | A1 | 11/2016 | Dayton |
| 2017/0172396 | A1 | 6/2017 | Nguyen et al. |
| 2018/0147309 | A1 | 5/2018 | Omidbakhsh |
| 2019/0023407 | A1 | 1/2019 | De Brito Teixeira |
| 2019/0070323 | A1 | 3/2019 | Atreya et al. |
| 2019/0328918 | A1* | 10/2019 | Conseil .................. A61L 2/206 |
| 2021/0008540 | A1* | 1/2021 | Procyshyn ............. C12M 37/02 |
| 2022/0151477 | A1 | 5/2022 | Morrison |
| 2022/0175994 | A1 | 6/2022 | Fryer |
| 2022/0226528 | A1 | 7/2022 | Fryer et al. |
| 2022/0378281 | A1 | 12/2022 | Hacker et al. |
| 2022/0387649 | A1 | 12/2022 | Fryer et al. |
| 2023/0397799 | A1 | 12/2023 | Nguyen |
| 2023/0417780 | A1 | 12/2023 | Childs et al. |

FOREIGN PATENT DOCUMENTS

| | | | |
|---|---|---|---|
| EP | 2586465 | B1 | 4/2014 |
| JP | 1992-51804 | Y2 | 10/1993 |
| JP | 1993-63187 | B2 | 9/1994 |
| JP | H8-24813 | A | 1/1996 |
| JP | 2010-011977 | A | 1/2010 |
| JP | 2017-524488 | A | 8/2017 |
| KR | 20190088628 | A | 7/2019 |
| WO | 2005011747 | A2 | 2/2005 |
| WO | 2007014436 | A1 | 2/2007 |
| WO | 2010000022 | A1 | 1/2010 |
| WO | 2010006355 | A1 | 1/2010 |
| WO | 2017185138 | A1 | 11/2017 |
| WO | 2019113634 | A1 | 6/2019 |
| WO | 2019113635 | A1 | 6/2019 |
| WO | 2020077403 | A1 | 4/2020 |
| WO | 2020077406 | A1 | 4/2020 |
| WO | 2022011430 | A1 | 1/2022 |

OTHER PUBLICATIONS

International Preliminary Report on Patentability issued in PCT/US2022/030931, dated Dec. 7, 2023.
International Search Report and Written Opinion issued in PCT/US2022/030931, mailed Apr. 19, 2022, 9 pages.
Supplementary European Search Report issued in EP 17870809.5, issued Jul. 16, 2020.
International Search Report and Written Opinion Issued in PCT/CA2017/051362, dated Feb. 1, 2018.
International Search Report and Written Opinion Issued in PCT/US2023/13045, dated Apr. 27, 2023, 9 pages.
Extended European Search Report Issued in EP22812073.9, dated Feb. 14, 2025.

* cited by examiner

PORT CONNECTORS

CROSS-REFERENCE TO RELATED APPLICATION

This application claims priority to U.S. Provisional App. No. 63/193,377, filed May 26, 2021, the entirety of which is hereby incorporated by reference.

FIELD

The present disclosure generally relates to port connectors, and, more specifically, to port connectors for sterilizing the surfaces of a fluid port.

BACKGROUND

Certain articles, such as medical devices (e.g., endoscopes), need to be sterilized between uses. These articles can include interior lumens, which require sterilization. One way to sterilize these interior lumens is to move a sterilization fluid or sterilant through the lumens. In order to move the sterilization fluid through the lumen, a port connector is typically coupled to a fluid port of the article.

For example, PCT Publication No. WO 2018/090133 describes a sterilization system where an endoscope is placed within a chamber with a port connector attached to a fluid port of the endoscope. The port connector fluidly couples the interior lumen(s) of the endoscope with a pressure source (e.g., negative pressure source). To sterilize the interior lumen(s) of the endoscope, a sterilization fluid (such as hydrogen peroxide vapor) is introduced into the chamber and then drawn through the interior lumen(s) of the endoscope via the pressure source fluidly coupled to endoscope by a port connector.

SUMMARY

In one aspect, a port connector for connecting to a fluid port of a device to be sterilized to a sterilization apparatus is disclosed. The fluid port has a distal end defining a fluid port outlet. The fluid port defines a lumen extending proximally from the fluid port outlet. The port connector comprises a housing configured to couple to the fluid port. The housing defines an inlet configured to be fluidly coupled to the lumen of the fluid port, an outlet configured to be fluidly coupled to the sterilization apparatus, and a fluid passageway extending between and fluidly coupling the inlet and outlet. A porous member is supported by the housing. The porous member has a porous structure defining a plurality of minute passageways. The porous member is arranged relative to the housing to engage the distal end of the fluid port when the port connector is connected to the fluid port.

In another aspect, a method of sterilizing a device having a fluid port comprises connecting a port connector to the fluid port. The port connector defines an inlet in fluid communication with the fluid port, an outlet and a fluid passageway extending between the fluidly connecting the inlet and outlet. The port connector has a porous member that engages an end of the fluid port. The method includes fluidly connecting a sterilization apparatus to the outlet of the port connector and sterilizing the end of the fluid port while the port connector is connected to the fluid port by moving a sterilization fluid through the porous member.

In another aspect, a port connector for connecting a fluid port of a device to be sterilized to a sterilization apparatus comprises a housing configured to couple to the fluid port.

The housing defines an outlet configured to be fluidly coupled to the sterilization apparatus. A seal is arranged to form a fluid tight seal with the fluid port. A piston is supported by the housing and is movable relative to the housing upon the application of a pressure differential by the sterilization apparatus.

In another aspect, a port connector for connecting to a fluid port of a device to be sterilized to a sterilization apparatus, the fluid port defining a lumen, comprises a porous member having a porous structure defining a plurality of minute passageways. The porous member defines at least a portion of a receiving chamber sized and shaped to receive the fluid port. The interior surface is arranged to engage the fluid port when the fluid port is disposed in the receiving chamber. A housing is coupled to the porous member. The housing defines an inlet configured to be fluidly coupled to the lumen of the fluid port, an outlet configured to be fluidly coupled to the sterilization apparatus, and a fluid passageway extending between and fluidly coupling the inlet and outlet. The inlet is disposed in said at least a portion of the receiving chamber defined by the interior surface of the porous member.

Other object and features of the present disclosure will be in part apparent and in part pointed out herein.

BRIEF DESCRIPTION OF THE DRAWINGS

Corresponding reference characters indicate corresponding parts throughout the drawings.

DETAILED DESCRIPTION

The port connectors disclosed herein can be used with the sterilization system and method described in PCT Publication No. WO 2018/090133. The port connectors described herein enable the fluid ports themselves to be sterilized even with a port connector attached thereto. The port connectors permit the sterilization fluid to come into contact with interior and/or exterior surfaces of the fluid ports that would otherwise be blocked or covered using conventional port connectors, thus enabling generally the entire fluid port to be sterilized, and more specifically the exterior or exposed surfaces closest to the lumen of the fluid port as these surfaces are most likely to come into contact with a fluid flowing through the fluid port. The port connectors disclosed herein may be referred to as leaky connectors because the port connectors may not form a fluid tight seal with the fluid port and/or may only form a fluid tight seal with the fluid port under certain conditions.

Figure 1:
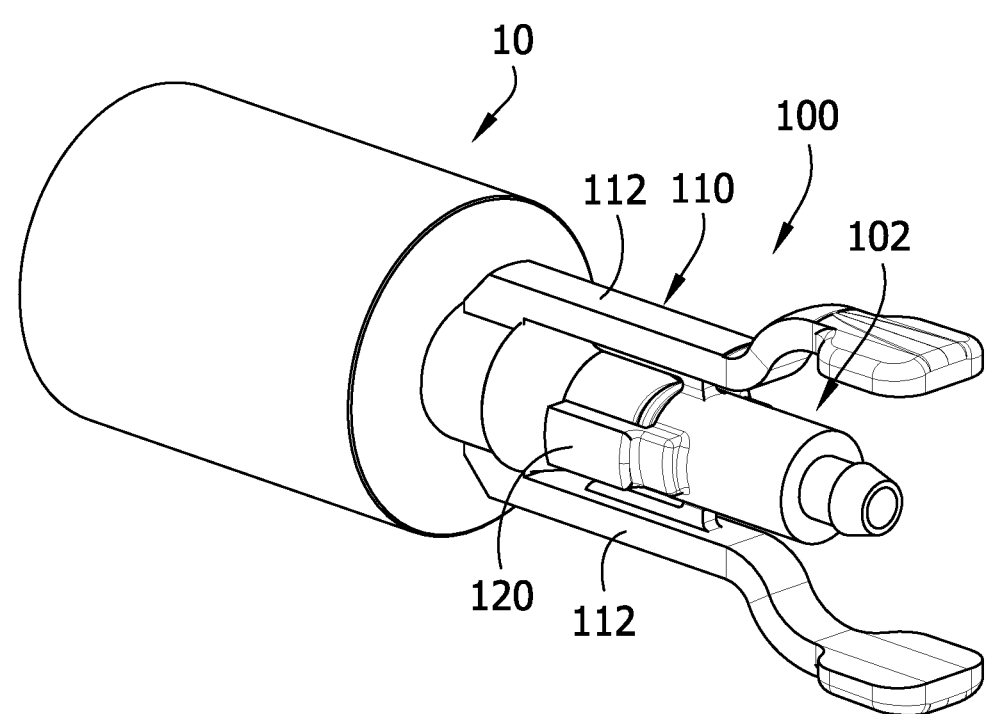
FIG. 1 is a perspective of a port connector according to one embodiment of the present disclosure connected to a fluid port.
Figure 2:
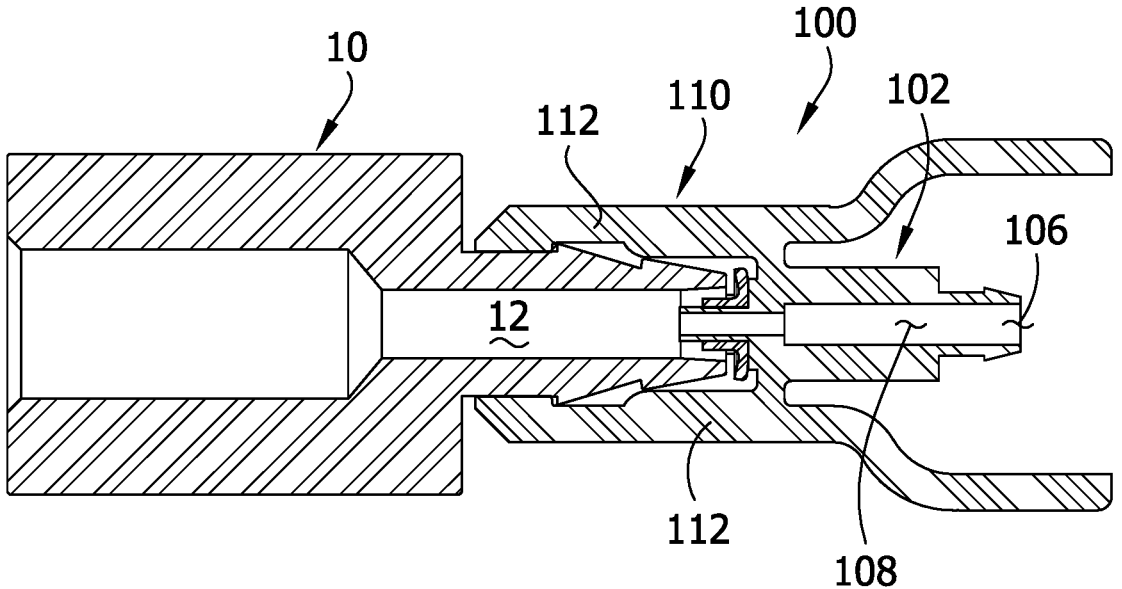
FIG. 2 is a longitudinal cross-section thereof.
Figure 3:
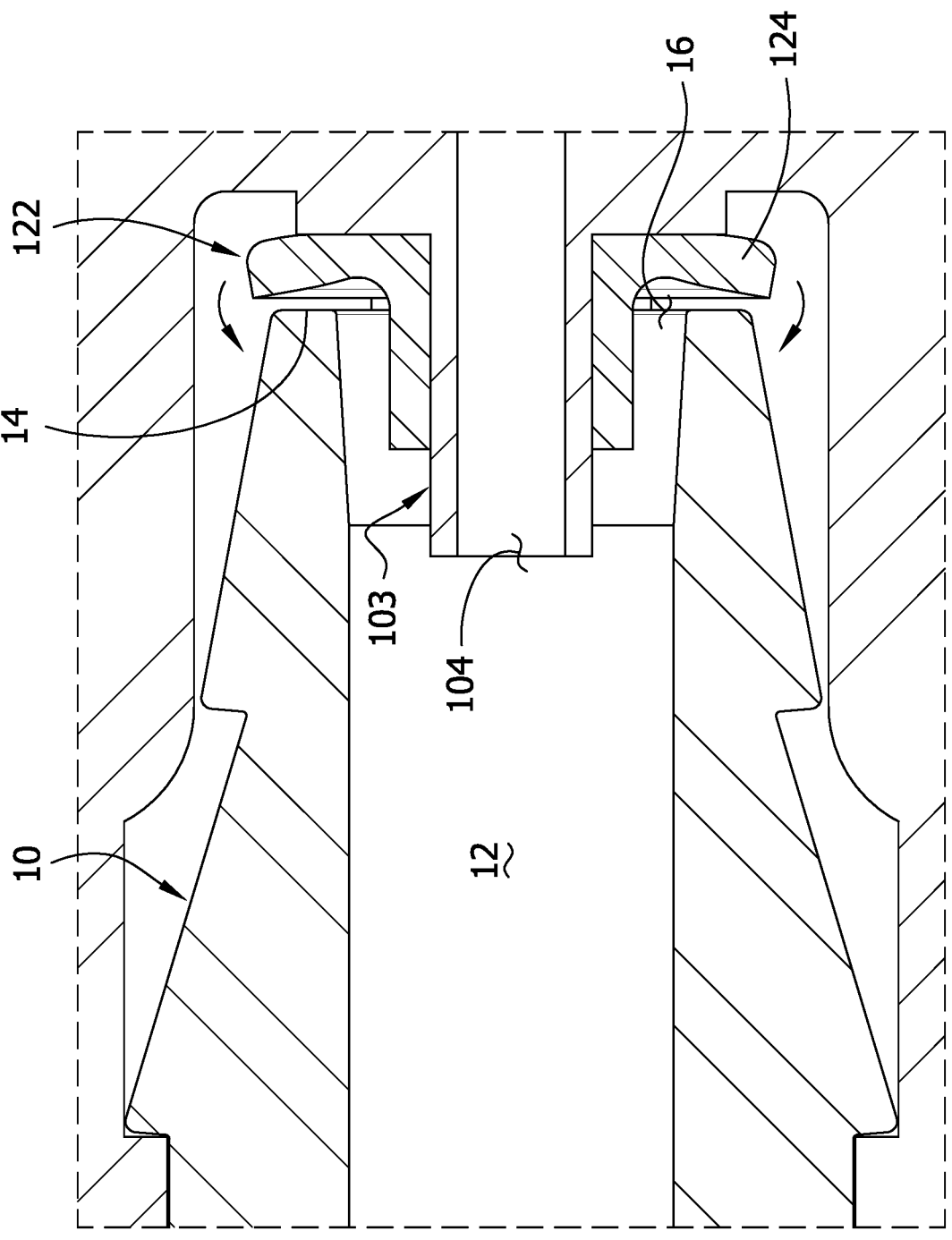
FIG. 3 is an enlarged, fragmentary view of FIG. 2.
Figure 4:
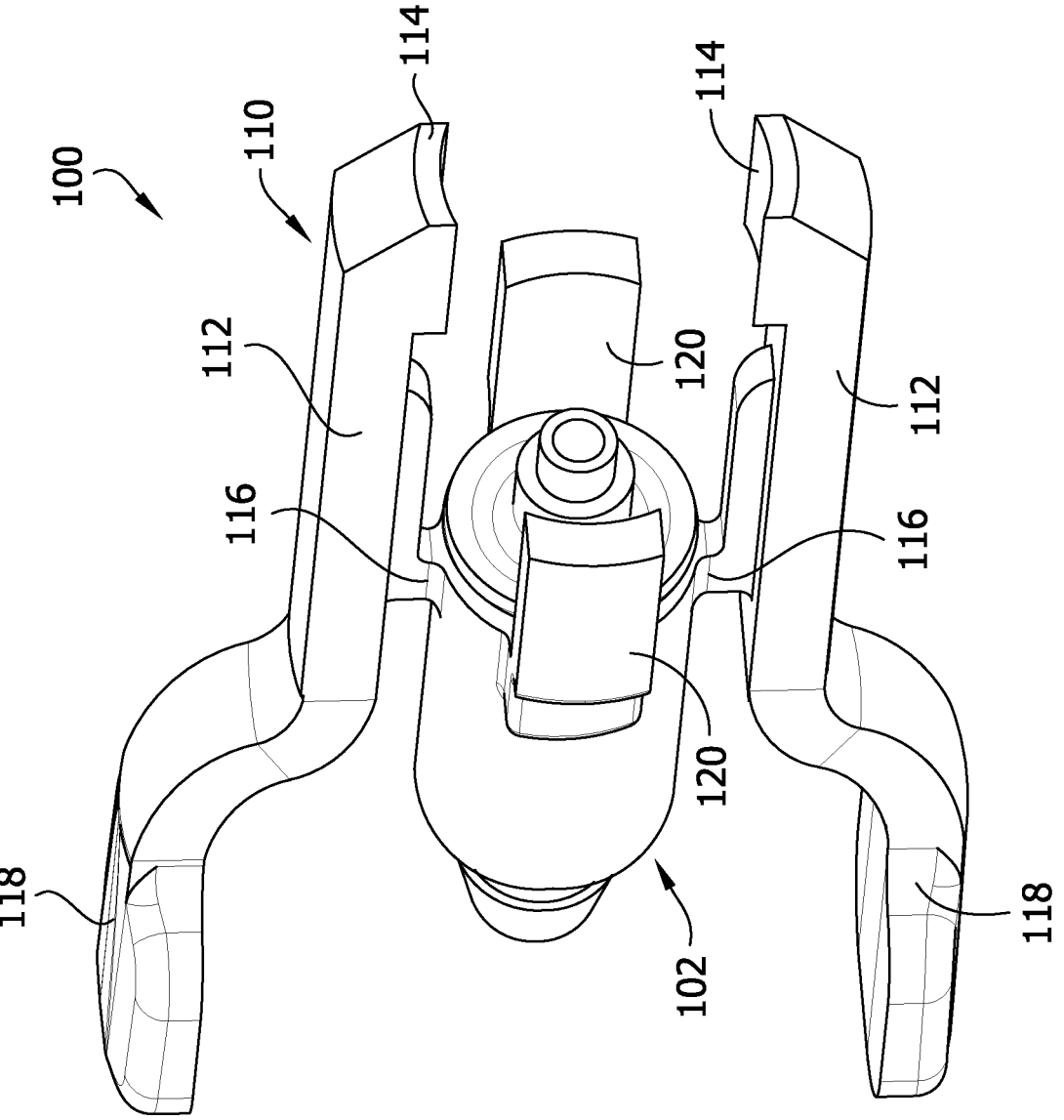
FIG. 4 is a perspective of the port connector of FIG. 1.

Referring to FIGS. 1-6, one embodiment of a port connector according to the present disclosure is generally indicated by reference numeral 100. The port connector 100 is shown attached to a fluid port 10 of an article (not shown), such as an endoscope. The illustrated fluid port 10 is a male fluid port having one or more circumferential barbs on the exterior for facilitating connection and sealing of components and devices (such a tubes) to the fluid port, as generally known in the art. As shown in FIGS. 2 and 3, the fluid port defines a fluid port outlet 16 at the end (e.g., distal or free end) thereof and a lumen 12 extending proximally from the fluid port outlet. The fluid port 10 has a distal end surface 14 (broadly, an exterior surface) at the end. The distal end surface 14 faces distally and borders the fluid port outlet 16. Other configurations of the fluid port are within the scope of the present disclosure. The port connector 100 is used for connecting the fluid port 10 of an article or device to be sterilized (via a sterilization fluid) to a pressure source (e.g., a negative pressure source and/or a positive pressure source) of a sterilization system or apparatus (not shown), such as the sterilization system described in PCT Publication No. WO 2018/090133. In one embodiment, the pressure source is a negative pressure source that creates a pressure differential to draw fluid (e.g., a sterilization fluid) from the environment surrounding the article and port connector 100, into interior lumen(s) of the article and through the fluid port 10 and port connector to sterilize the interior surfaces (e.g., interior lumen(s)) of the article. The negative pressure source can be any suitable pressure source such as a vacuum, a pump, or a chamber having a lower pressure then the environment surrounding the article.

The port connector 100 includes a housing 102. The housing 102 has a proximal end portion and a distal end portion. The proximal end portion defines an inlet 104 (FIG. 3) configured to be fluidly coupled to the fluid port (e.g., the inlet is arranged to be in fluid communication with the fluid port). In the illustrated embodiment, the proximal end portion includes an insertion portion 103 sized and shaped to be inserted through the fluid port outlet 16 and into a lumen 12 of the fluid port 10, such that the inlet 104 is disposed in the lumen. The insertion portion 103 defines the inlet 104. Preferably, the insertion portion 103 does not engage the fluid port 10. The distal end portion (e.g., distal port) defines an outlet 106 configured to be fluidly coupled to the negative pressure source (broadly, the sterilization apparatus). In other words, the outlet 106 is arranged to be in fluid communication with the negative pressure source. In the illustrated embodiment, the distal end portion is configured to be coupled to a fluid conduit or tube to fluidly couple the outlet 106 to the negative pressure source. The distal end portion comprises a barbed tube port fitting. The housing 102 defines a fluid passageway 108 (e.g., lumen, bore) extending between and fluidly coupling (e.g., providing fluid communication between) the inlet 104 and the outlet 106.

The housing 102 is configured to be coupled to the fluid port 10. The housing 102 includes a coupler 110 configured to couple to (e.g., mount on) the fluid port 10. In the illustrated embodiment, the coupler 110 comprises first and second resiliently deflectable clips 112. The first and second clips 112 are configured to engage the fluid port 10 to couple (e.g., secure) the port connector 100 to the fluid port. Each clip 112 includes a retainer 114 configured to engage the fluid port 10 to secure the port connector 100 to the fluid port. The retainers 114 engage a barb of the fluid port 10 to secure the coupler 110 to the fluid port. The clips 112 are disposed on opposite sides of the housing 102 to engage opposite sides of the fluid port 10. The housing 102 includes a living hinge 116 connecting each clip 112 to the rest of the housing (e.g., a central body). The living hinges 116 permit each clip 112 to resiliently deflect so that the coupler can be attached and detached from the fluid port. The living hinges 116 bias the retainers 114 toward each other, so that the port connector 100 does not unintentionally disconnect from the fluid port 10. Each clip 112 includes a finger tab 118 configured to be engaged by a user to deflect or pivot the clip about the living hinge 116. Other configurations of the coupler are within the scope of the present disclosure. The housing 102 may also include one or more port guides 120 configured to engage the fluid port 10 and help center the port connector 100 on the fluid port. In the illustrated embodiment, the housing 102 includes two port guides 120 disposed on opposite sides of the housing 102, in between the two clips 112, to engage opposite sides of the fluid port 10. The opposing inner faces of the port guides 120 may engage the fluid port 10 to facilitate positioning of the port connector 100 on the fluid port 10. The housing 102 may be a one-piece component or multiple components secured together. The guides 120 and/or clips 112 (broadly, the port connector 100) define a space sized and shaped to receive the end portion of the fluid port 10.

Figure 5:
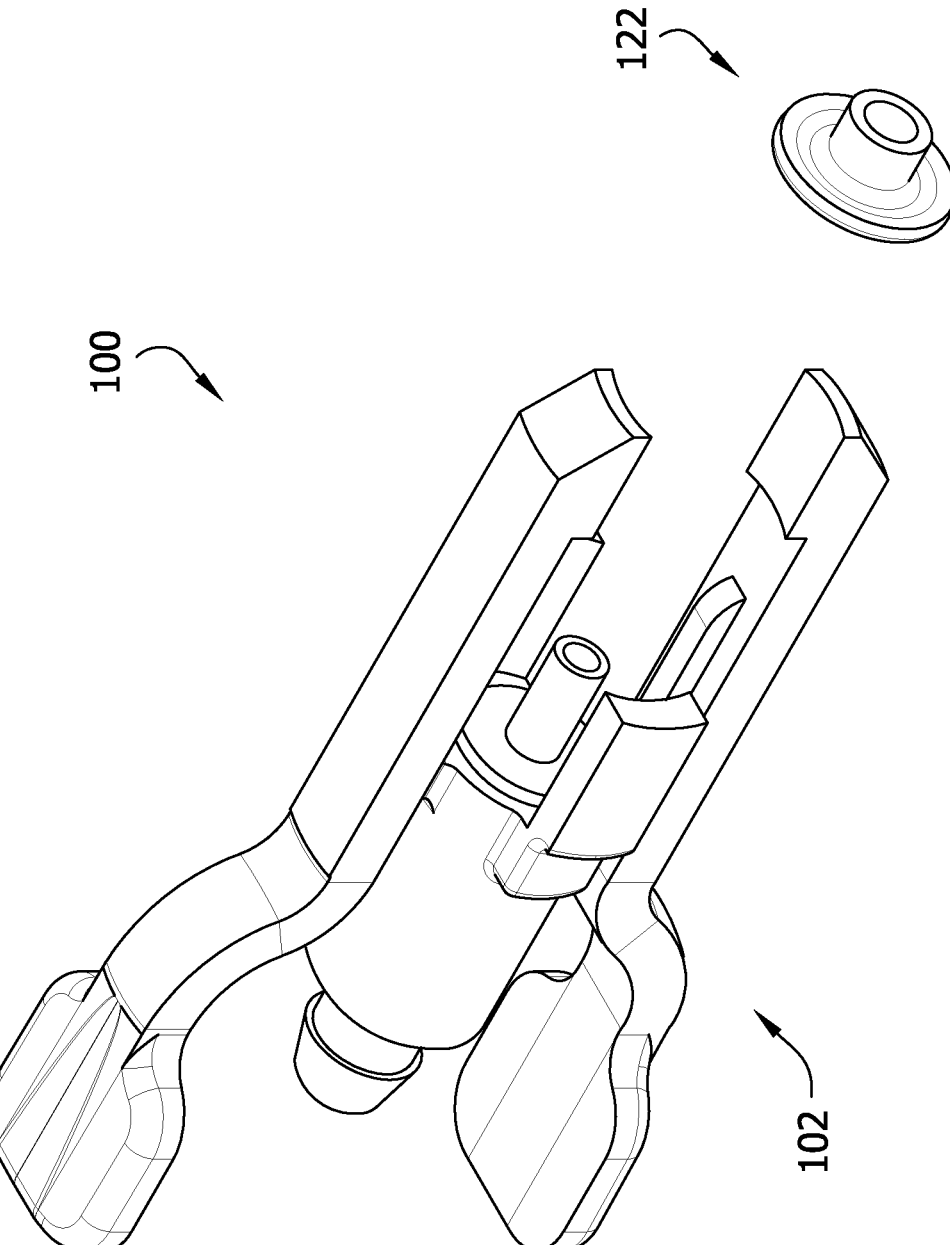
FIG. 5 is an exploded view of the port connector of FIG. 1.
Figure 6:
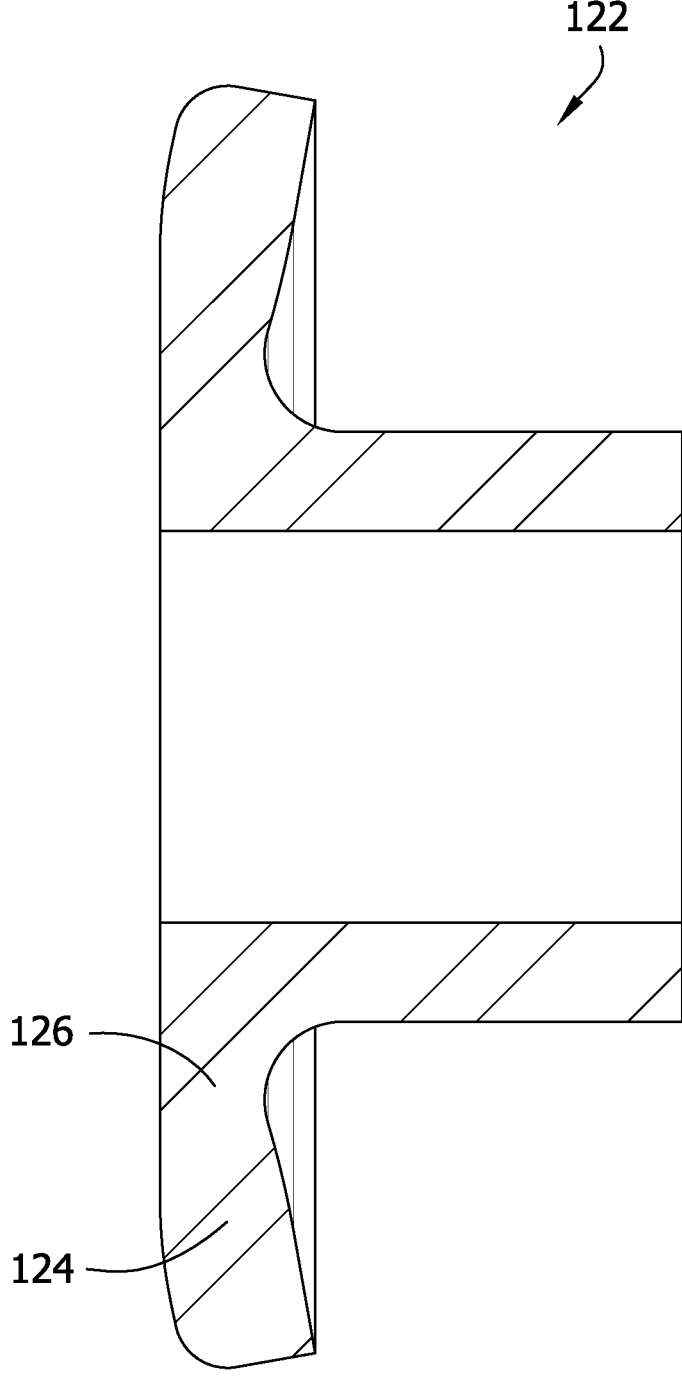
FIG. 6 is a cross-section of a gasket of the port connector of FIG. 1.
Figure 7:
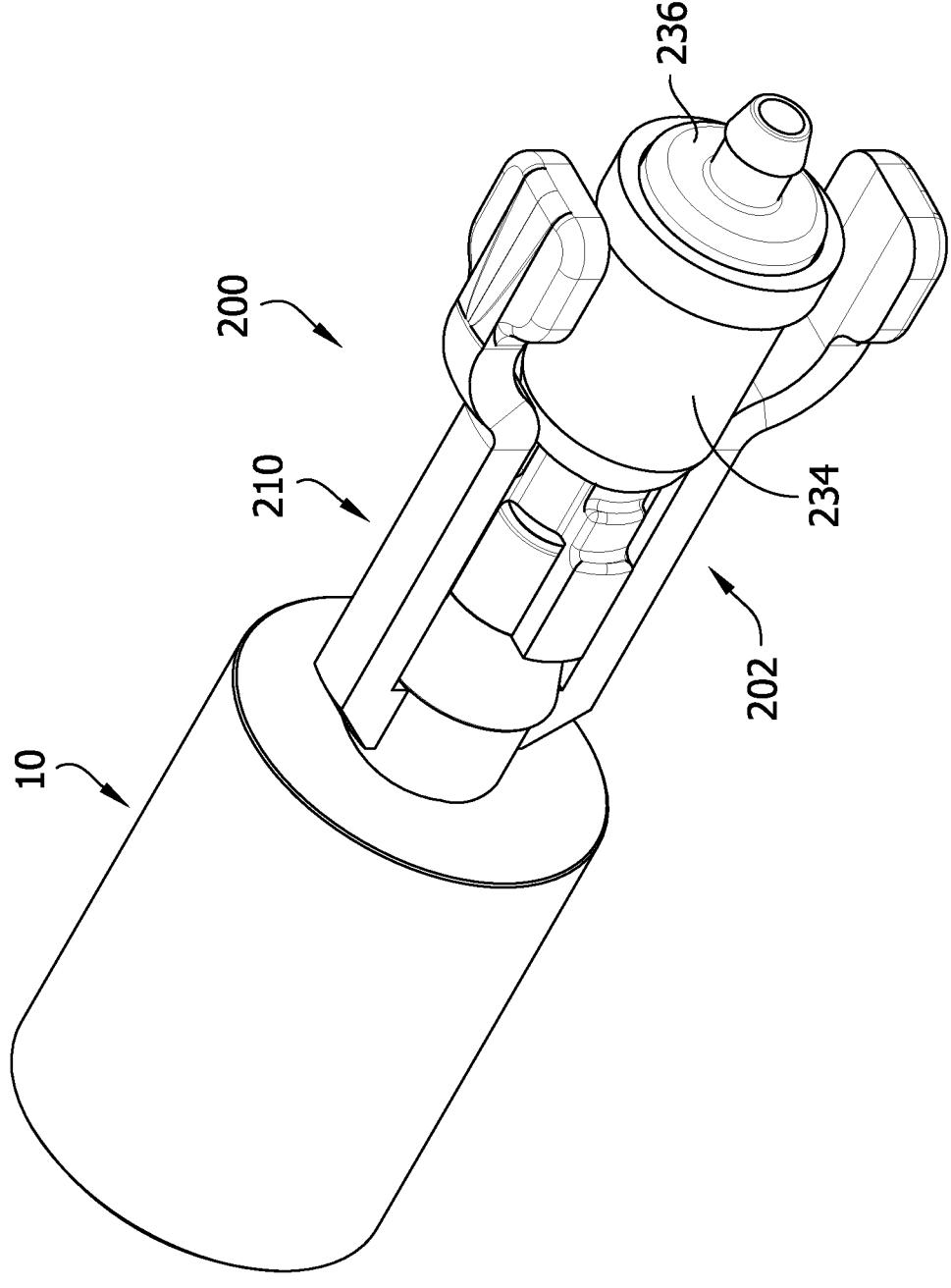
FIG. 7 is a perspective of a port connector according to another embodiment of the present disclosure connected to a fluid port.

Referring to FIGS. 3, 5 and 6, the port connector 100 includes a seal or gasket 122 (broadly, a fluid port interface member). The gasket 122 is supported by (e.g., connected to) the housing 102. As shown in FIG. 3, the gasket 122 is supported by the housing 102 such that the gasket is spaced part from the fluid port 10 when the housing is coupled to the fluid port. Specifically, the gasket 122 is arranged to face and be adjacent to the distal end surface 14 of the fluid port 10, when the port connector 100 is attached to the fluid port. The guides 120 may also act as a stop that engage the fluid port 10 to position (e.g., longitudinally or proximally position) the gasket 122 adjacent the distal end surface 14. When the port connector 100 is attached to the fluid port 10, the port connector 100 (e.g., gasket 122) does not form a fluid tight seal with the fluid port. This permits the sterilization fluid in the environment surrounding the fluid port 10 of the article to come into contact with and sterilize surfaces (e.g., the end surface 14) of the fluid port that would otherwise be blocked or covered when the port connector 100 engages the fluid port to form a fluid tight seal.

The port connector 100 forms a fluid tight seal with the fluid port 10 when negative pressure (i.e., a negative pressure differential) is applied to the lumen 12 of the fluid port, via the negative pressure source. This ensures that the fluid (e.g., sterilization fluid) is drawn into the interior lumen(s) of the article and through the fluid port 10 to sterilize the article. The gasket 122 is configured to move toward and engage the fluid port 10 to form the fluid tight seal upon the application of negative pressure from the negative pressure source in order to draw fluid through the fluid port. The term "fluid tight seal" as used herein refers to a seal that creates a sufficient impediment to the flow of fluid such that fluid flows from other areas (e.g., into the end of interior lumen(s) of the article opposite the fluid port) as a result of a pressure differential and does not require an absolute fluid tight seal such that no fluid can pass. For instance, the fluid tight seal between the gasket 122 and the fluid port 10 must form a sufficient impediment to the flow of fluid therebetween such that fluid is drawn into and through the interior lumen(s) of the article, through the fluid port and into the port connector 100. In operation, preferably, the gasket 122 forms an absolute fluid tight seal with the fluid port 10 such that no fluid can pass therebetween, but such an absolute flight tight seal is not required for the operation of the port connector 100. As used herein, the phrase "negative pressure" means a pressure that is lower than a pressure of the environment surrounding the relative component(s) to which the negative pressure is being applied, such as the port connector 100. For example, applying negative pressure from a negative pressure source to the port connector 100 means the negative pressure source imparts a low pressure on the port connector relative to the pressure in the environment surrounding the port connector (e.g., the chamber of the sterilization system in which the port connector is positioned). In other words, the negative pressure creates a negative pressure differential between the environment surrounding the relative components and the negative pressure source, thereby causing fluid to flow from the environment toward the negative pressure source. A negative pressure can be a pressure at or above atmospheric pressure or a pressure below atmospheric pressure (vacuum). In certain preferred embodiments, a negative pressure is below atmospheric pressure (vacuum).

In the illustrated embodiment, the gasket 122 includes a flange 124. The flange 124 is bendable (e.g., resiliently bendable). The flange 124 has a ring-shape. The flange 124 is configured to move toward (as indicated by the arrows in FIG. 3) and engage the fluid port 10 (e.g., end surface 14) to form the fluid tight seal with the fluid port due to the application of negative pressure. The flange 124 is disposed adjacent the end surface 14 of the fluid port 10 when the port connector 100 is attached to the fluid port. For example, the flange 124 may only be spaced apart from the end surface 14 by a few millimeters. As a result, when negative pressure is applied by the negative pressure source, the negative pressure (e.g., a sufficient pressure differential created across the flange 124) causes the flange to bend and engage the end surface of the fluid port 10 to create the fluid tight seal. In one embodiment, the pressure differential between the negative pressure source and the environment surrounding the article may be at a ratio of about $\frac{1}{100}$, although other differentials are within the scope of the present disclosure. The flange 124 preferably extends radially outward of the portion of the housing 102 adjacent the flange such that a radially outward portion of the flange (e.g., distal surface) is exposed to the environment to increase the effect of the pressure differential on the flange. The flange 124 may include a bending section 126 where a majority of the bending of the flange occurs. In the illustrated embodiment, the bending section is adjacent the radially inward edge of the flange 124 and has a thickness less than a thickness of more radially outward portions of the flange. Thus, a point a weakness in the flange 124 is created, about which the flange can bend. The flange 124 is resiliently deformable such that once the pressure differential moves closer to equilibrium (or at equilibrium), the flange 124 returns to its undeformed or unbent state, as shown in FIG. 3. For example, the flange 124 may be designed to return to its unbent state when the pressure differential is about half of the pressure differential initially imparted by the negative pressure source. Accordingly, the flange 124 can be configured to disengage from the fluid port 10 and break the fluid tight seal at a specific pressure differential or over pressure differential range.

In operation, to sterilize an article having the fluid port 10, the port connector 100 is connected to the fluid port. As mentioned above, the gasket 122 is spaced apart from the fluid port 10 when the port connector 100 is initially connected to the fluid port (e.g., before the fluid tight seal is formed). The negative pressure source is fluidly connected to the port connector 100 (e.g., outlet 106). The article with the fluid port 10 is placed in a chamber (e.g., cleaning chamber). A fluid (e.g., sterilization fluid) is supplied or introduced into the chamber. The fluid may remain in the chamber for a period of time, such as 5-10 minutes, before applying the negative pressure. During this time, the fluid may naturally move or be forcefully moved around the chamber and come into contact with and sterilize surfaces of the article and fluid port, such as surfaces that will become blocked or covered when the port connector 10 forms the fluid tight seal with the fluid port. Then, the operator applies the negative pressure via the negative pressure source. As a result, a fluid tight seal is formed between the port connector 100 and the fluid port 10 (e.g., end surface 14) by moving the gasket 122 (e.g., flange 124) toward and into engagement with the fluid port. As described above, the fluid tight seal is formed by bending the flange 124. Moreover, the application of negative pressure moves (e.g., draws) fluid into and through the interior lumen(s) of the article and through the fluid port 10 and the port connector 100, thereby sterilizing the interior of the article. Thus, even though the port connector 100 is attached to the fluid port 10 during the sterilization process, generally the entire fluid port is exposed to the sterilization fluid at some point and sterilized.

Referring to FIGS. 7-14, another embodiment of a port connector according to the present disclosure is generally indicate by reference numeral 200. The port connector 200 of FIGS. 7-14 is generally analogous to the port connector 100 of FIGS. 1-6 and thus, for ease of comprehension, where similar, analogous or identical parts are used, reference numerals "100" units higher are employed. Accordingly, unless clearly stated or indicated otherwise, the above descriptions regarding the port connector 100 of FIGS. 1-6 also apply to the port connector 200 of FIGS. 7-14.

In this embodiment, the housing 202 includes a piston or plunger 230, a connector body 232, a sleeve or slide 234 and a cap 236. The cap 236 defines the outlet 206 and is configured to be coupled to a fluid conduit or tube to fluidly couple the outlet to the negative pressure source. The plunger 230 defines the insertion portion 203 and the inlet 204. The gasket 222 is supported by the plunger 230. The connector body 232 defines a longitudinal bore 238 extending therethough. The plunger 230 is movably (e.g., slidably) disposed within the longitudinal bore 238. The port connector 200 may include a seal 240, such as an O-ring, disposed between the plunger 230 and the connector body 232 to prevent the flow of fluid between the plunger and connector body. In the illustrated embodiment, the seal 240 may also function as a stop that the plunger 230 engages to limit the distal movement of the plunger relative to the connector body 232. The slide 234 is movably (e.g., slidably) supported by (e.g., mounted on) the connector body 232. The slide 234 includes a circumferential wall 242 that surrounds and moves relative to a cylindrical portion of the connector body 232. Thus, the circumferential wall 242 defines a cavity sized and shaped to receive the distal end of the connector body 232. The port connector 200 may include one or more seals 244, such as O-rings, disposed between the slide 234 (e.g., circumferential wall 242) and the connector body 232 (e.g., cylindrical portion) to prevent the flow of fluid between the slide and the connector body. One or both of the slide 234 and connector body 232 may define a groove sized and shaped to receive a portion of the seal 240. In the illustrated embodiment, the connector body 232 defines the groove. The cap 236 is secured to the slide 234 (e.g., a distal end thereof). The slide 234 and the plunger 230 are operatively coupled together such that movement of the slide results in movement of the plunger. In the illustrated embodiment, the plunger 230 is secured directly to the slide 234. The slide 234 defines a plunger recess 258 (FIG. 13) sized and shaped or receive the distal end of the plunger 230.

Figure 13:
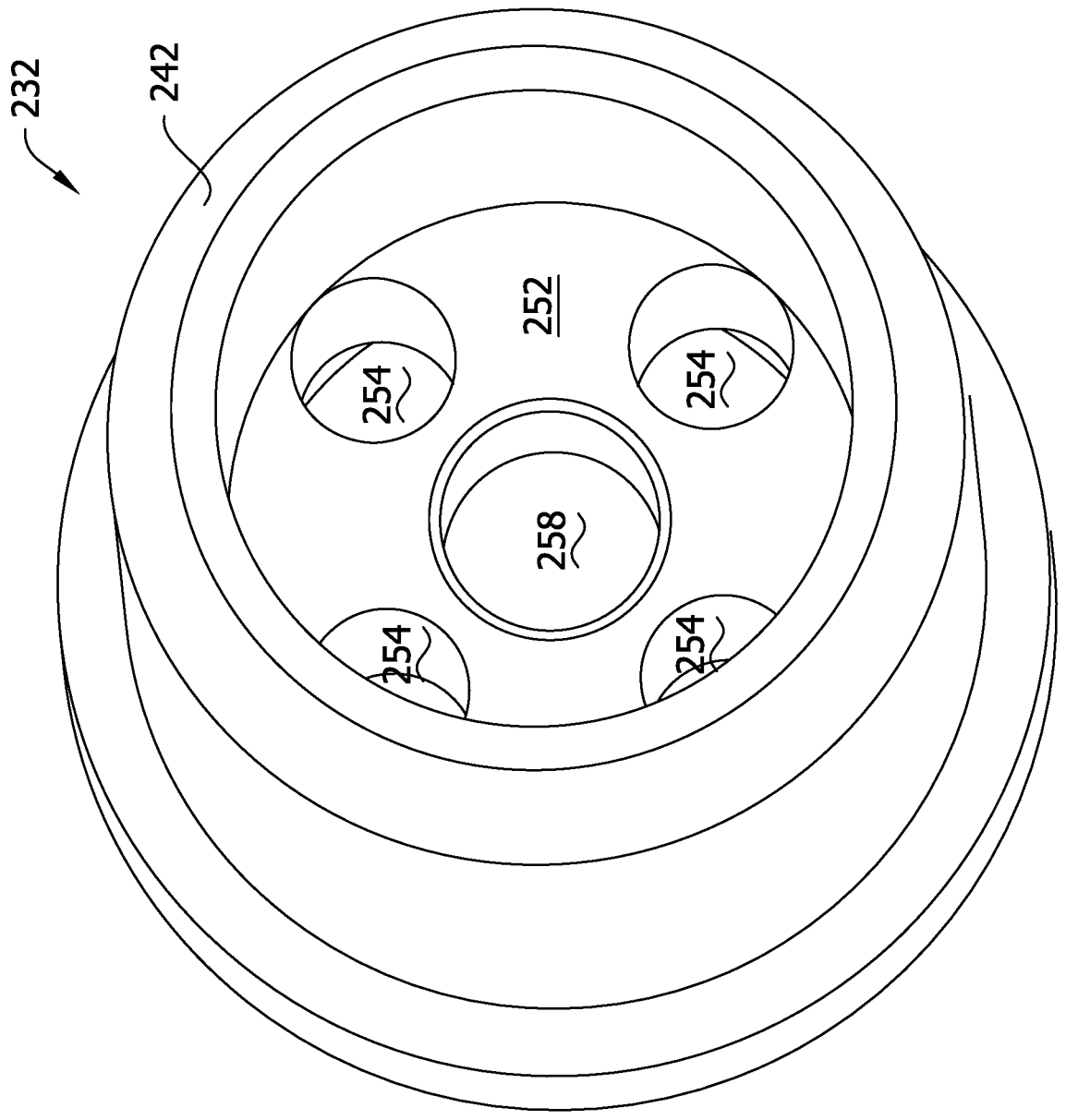
FIG. 13 is a perspective of a slide of the port connector of FIG. 7.

The plunger 230, the connector body 232, the slide 234 and the cap 236 define the fluid passageway 208. That is the plunger 230, the connector body 232, the slide 234 and the cap 236 each define a portion of the fluid passageway 208. Referring to FIG. 9, the portion of the fluid passageway 208 defined by the plunger 230 includes one or more plunger openings 246 and a plunger passageway (e.g., elongate bore) 248. The plunger passageway 248 extends between and fluidly couples the inlet 204 to the plunger openings 246. In the illustrated embodiment, the plunger 230 defines two plunger openings 246, on opposite sides of the plunger. The fluid passageway 208 includes a fluid chamber 250 defined by the housing 202. The one or more plunger openings 246 are in fluid communication (e.g., direct fluid communication) with the fluid chamber 250. As will be explained in more detail below, the fluid chamber 250 is configured to generally collapse or reduce in volume due to the application of negative pressure (i.e., a negative pressure differential). The fluid chamber 250 is at least partially defined by the connector body 232 and the slide 234. Specifically, the fluid chamber 250 is defined by a distal end of the connector body 232, the plunger 230, the circumferential wall 242 and a separation wall 252 of the slide 234. The portion of the fluid passageway 208 defined by the slide 234 includes at least one slide passageway 254 (FIG. 13). The slide passageway (s) 254 fluidly couple the fluid chamber 250 to the outlet 206. In the illustrated embodiment, the slide 234 includes four slide passageways 254. The slide 234 and cap 236 define an outlet chamber 256 (FIG. 8) fluidly coupled to the outlet 206. The slide passageways 254 extend between and fluidly connect the outlet chamber 256 and the fluid chamber 250, with are on opposite sides of the separation wall 252.

Figure 9:
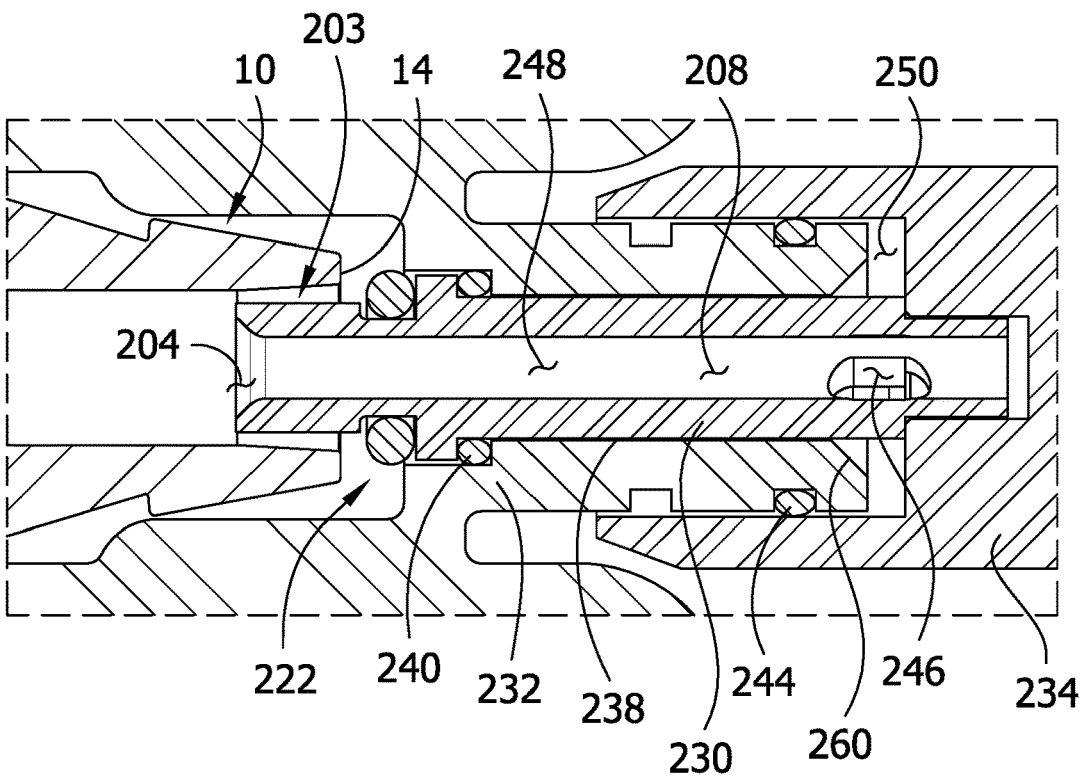
FIG. 9 is an enlarged, fragmentary view of FIG. 8, with a gasket of the port connector in an initial position.
Figure 10:
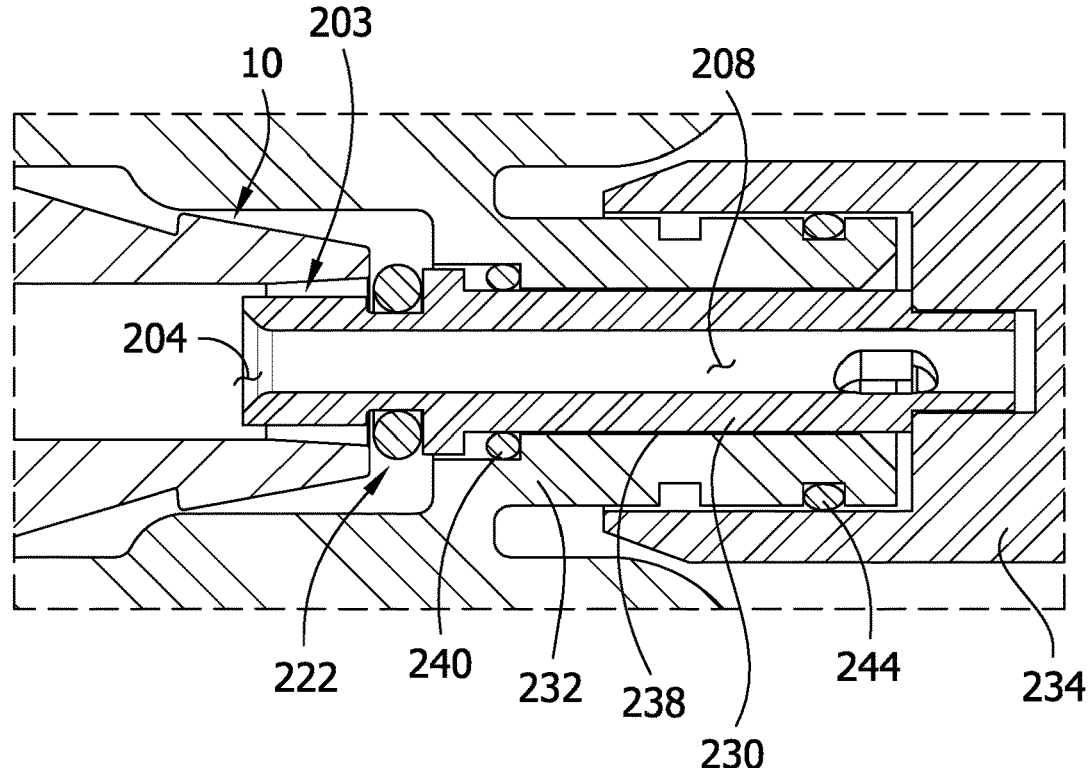
FIG. 10 is an enlarged, fragmentary view of FIG. 8, with the gasket in a sealing position.
Figure 11:
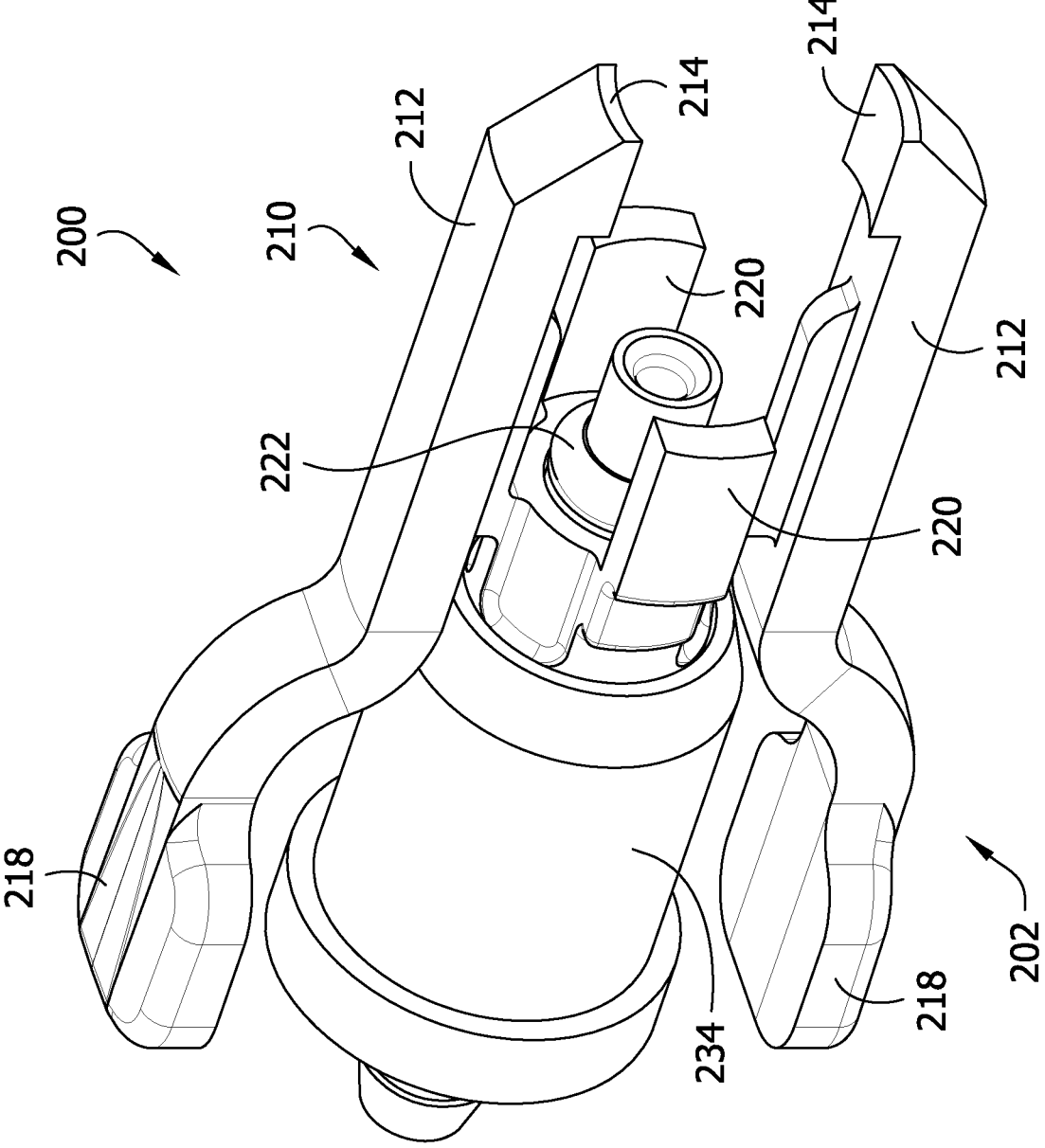
FIG. 11 is a perspective of the port connector of FIG. 7.
Figure 12:
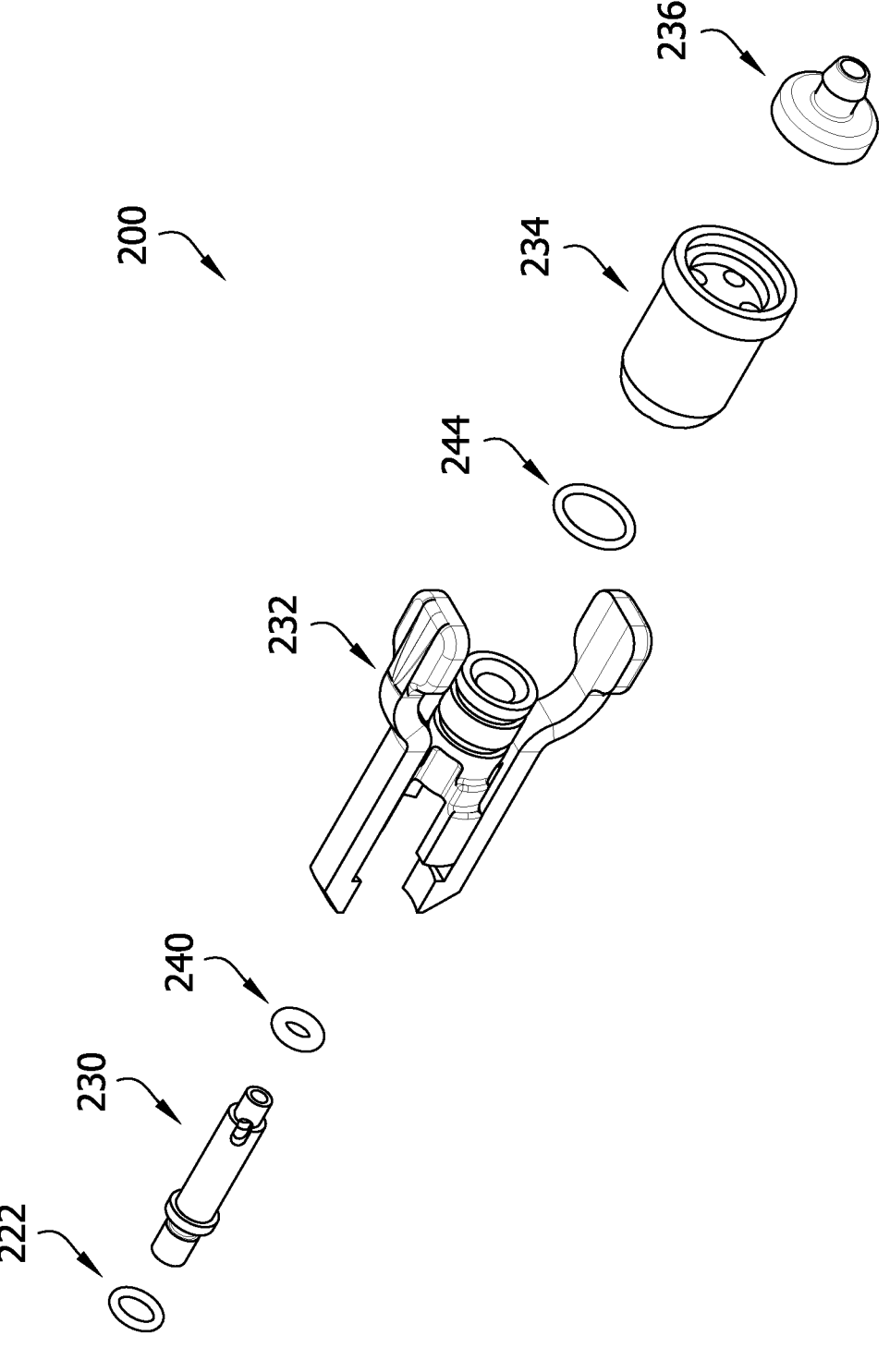
FIG. 12 is an exploded view of the port connector of FIG. 7.

The plunger 230 is configured to move proximally or toward the fluid port 10 upon the application of pressure differential (i.e., negative pressure), along the longitudinal bore 238, to move the gasket 222 toward the fluid port 10 (e.g., end surface 14) so that the gasket engages the fluid port to form the fluid tight seal with the fluid port. Specifically, the slide 234 moves proximally relative to the connector body 232 due to the application of negative pressure from the negative pressure source to generally reduce in volume (e.g., collapse) the fluid chamber 250 (FIG. 10). As a result of the proximal movement of the slide 234, the plunger 230 moves proximally (from the initial position shown in FIG. 9) to move the gasket 222 toward the fluid port 10 so that the gasket engages the fluid port (e.g., end surface 14) to form the fluid tight seal with the fluid port. FIG. 10 shows the gasket 222 in the sealing position, forming the fluid tight seal with the fluid port 10, after the application of negative pressure. Preferably, the gasket 22 forms an absolute fluid tight seal with the fluid port 100. To facilitate the collapse of the fluid chamber 250, the combined cross-sectional area of the one or more slide passageways 254 is greater than the combined cross-sectional area of the plunger openings 246. Due to this configuration, the plunger openings 246 create a restriction in fluid flow (compared to the slide passageways 254), thereby facilitating the forming of a sufficient, localized negative pressure in the fluid chamber 250 to move the slide 234 proximally. Preferably, the plunger openings 246 are configured so that the plunger openings remain in fluid communication with the fluid chamber 250 when the plunger is moved proximally. In the illustrated embodiment, the distal end of the connector body 232 also includes a chamfer or bevel 260 at the distal end of the longitudinal bore 238 to keep the plunger openings 246 in fluid communication with the fluid chamber 250 when the plunger is moved proximally (e.g., in the sealing position).

In the illustrated embodiment, the resiliency (e.g., flexibility) of the gasket 222, the weight of the slide 234 and cap 236, and the weight of fluid conduit attached to the cap 236 generally keep the slide and plunger 230 in the initial position (FIG. 9) before the application of negative pressure, when the coupler 210 (e.g., clips 212, port guides 220) are attached to the fluid port 10. In one embodiment, the port connector 200 may include a spring (e.g., a coil spring) that may bias the slide 234 and plunger 230 distally, in the initial position.

Figure 14:
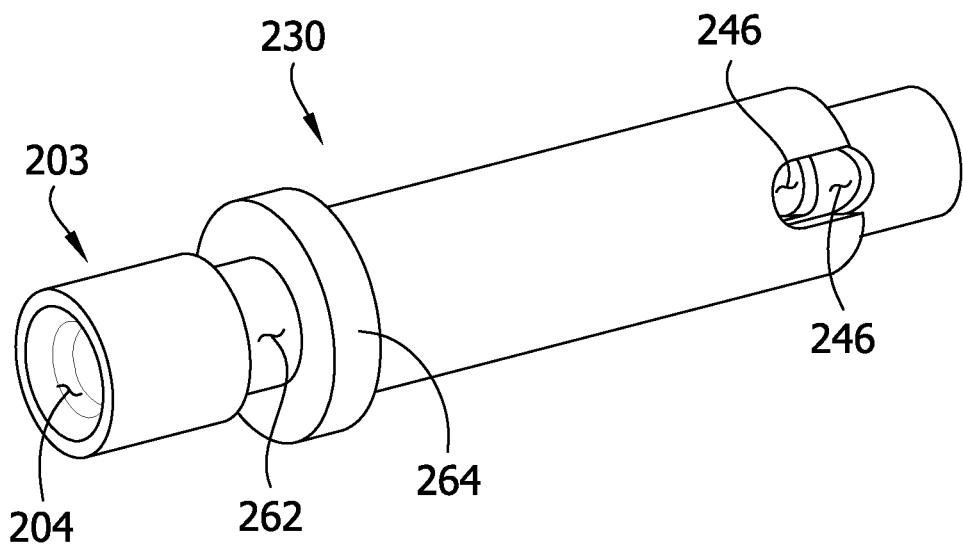
FIG. 14 is a perspective of a plunger of the port connector of FIG. 7.

Referring to FIG. 14, the plunger 230 is generally cylindrical. The plunger 230 defines a groove 262 in which the gasket 222 is disposed. The groove 262 is defined on a distal side by a radial or circumferential flange 264. The flange 264 braces the gasket 222 when the gasket engages the fluid port 10. The flange 264 is also arranged to engage the connector body 232, or more specifically the seal 240, to limit the distal movement of the plunger 230 (e.g., position the plunger and slide 234 in the initial position).

Figures 8, 8A:
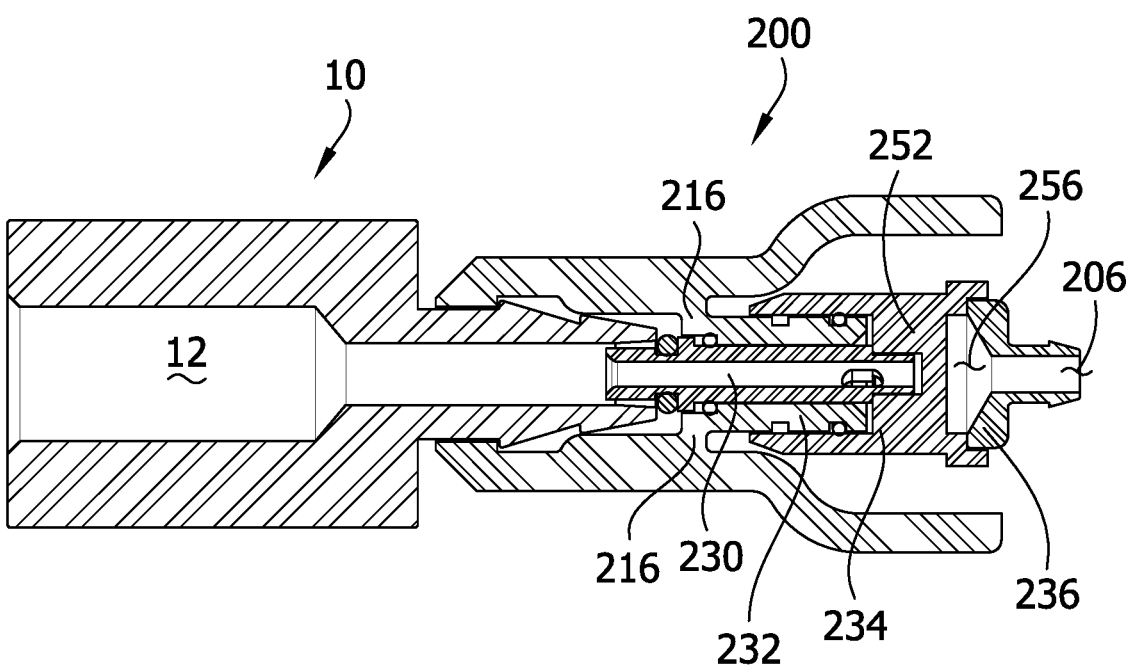
FIG. 8 is a longitudinal cross-section thereof.
FIG. 8A is a longitudinal cross-section of another embodiment of the port connector similar to the port connector of FIG. 7.

Referring to FIG. 8A, a version of the port connector without seals 240, 244 is generally indicated by reference numeral 200'. The port connector 200' of FIG. 8A is similar to the port connector 200 of FIG. 8 so that similar, analogous or identical elements are labeled with the same reference numerals, with the addition of a trailing prime. In this embodiment, the clearance between the outer surface of the connector body 232' and inner surface of the slide 234' is very small, which creates an ultra-low leak, low friction interface between the connector body and the slide that permits the slide to move relative to the connector body.

Similarly, the clearance between the inner surface of the connector body 232' defining the longitudinal bore 238' and the outer surface of the plunger 230' is also very small, again creating an ultra-low leak, low friction interface between the connector body and the plunger that permits the plunger to move relative to the connector body. The low leak interfaces between these components is sufficient to create a large enough resistance to fluid flow therebetween, such that when negative pressure is applied to the port connector 200', the slide 234' and the plunger 230' move proximally into the sealing position and draw fluid through the fluid port 10 as described herein in relation to the port connector 200 of FIG. 8. This occurs despite any fluid that may flow along these low leak interfaces. Accordingly, the port connector 200' of FIG. 8A generally functions and operates the same as the port connector 200 of FIG. 8.

In operation, to sterilize an article having the fluid port 10, the port connector 200 is connected to the fluid port. As mentioned above, the gasket 222 is spaced apart from the fluid port 10 when the port connector 200 is initially connected to the fluid port (e.g., before the fluid tight seal is formed). The negative pressure source is fluidly connected to the port connector 200 (e.g., outlet 206). The article with the fluid port 10 is placed in a chamber (e.g., cleaning chamber). A fluid (e.g., sterilization fluid) is supplied or introduced into the chamber. The fluid may remain in the chamber for a period of time, such as 5-10 minutes, before applying the negative pressure. During this time, the fluid may naturally move or be forcefully moved around the chamber and come into contact with and sterilize surfaces of the article and fluid port, such as surfaces that will become blocked or covered when the port connector 10 forms the fluid tight seal with the fluid port. Then, the operator applies the negative pressure via the negative pressure source. As a result, a fluid tight seal is formed between the port connector 200 and the fluid port 10 (e.g., end surface 14) by moving the gasket 222 toward and into engagement with the fluid port when connected to the fluid port by each clip 212 (e.g., retainer 214). As described above, moving the gasket 222 includes moving the plunger 230 and the slide 234. Specifically, the application of the negative pressure creates a vacuum in the fluid chamber 250 which moves the slide 234 proximally relative to the connector body 232. Moreover, the application of negative pressure moves (e.g., draws) fluid into the interior lumen(s) of the article and through the fluid port 10 and port connector 200, thereby sterilizing the interior of the article.

Figure 15:
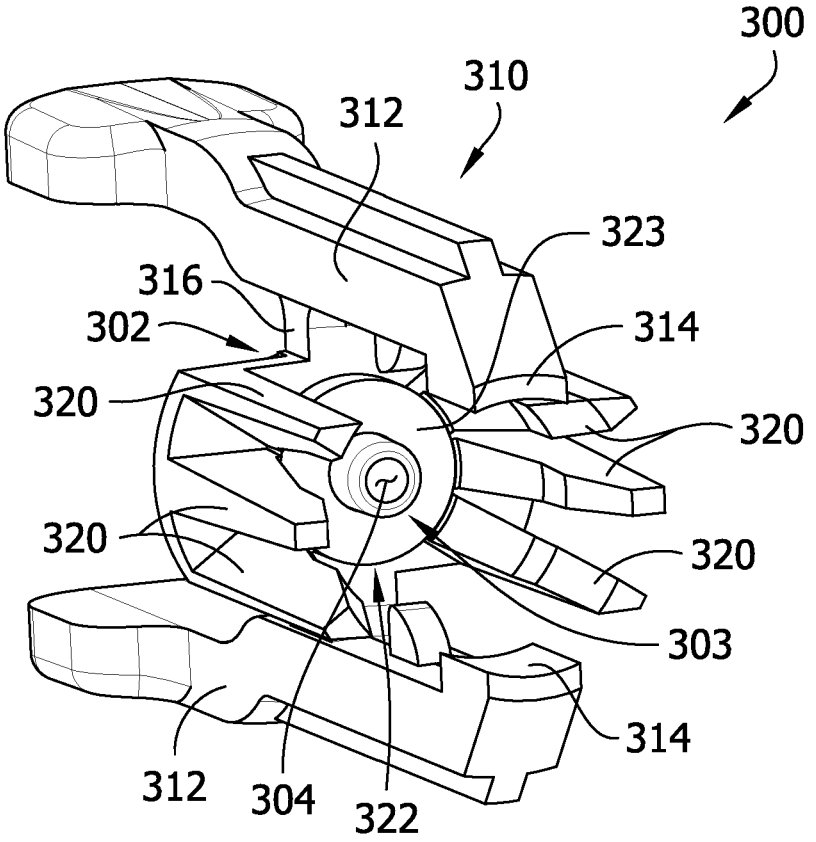
FIG. 15 is a perspective of a port connector according to another embodiment of the present disclosure.
Figures 16, 17:
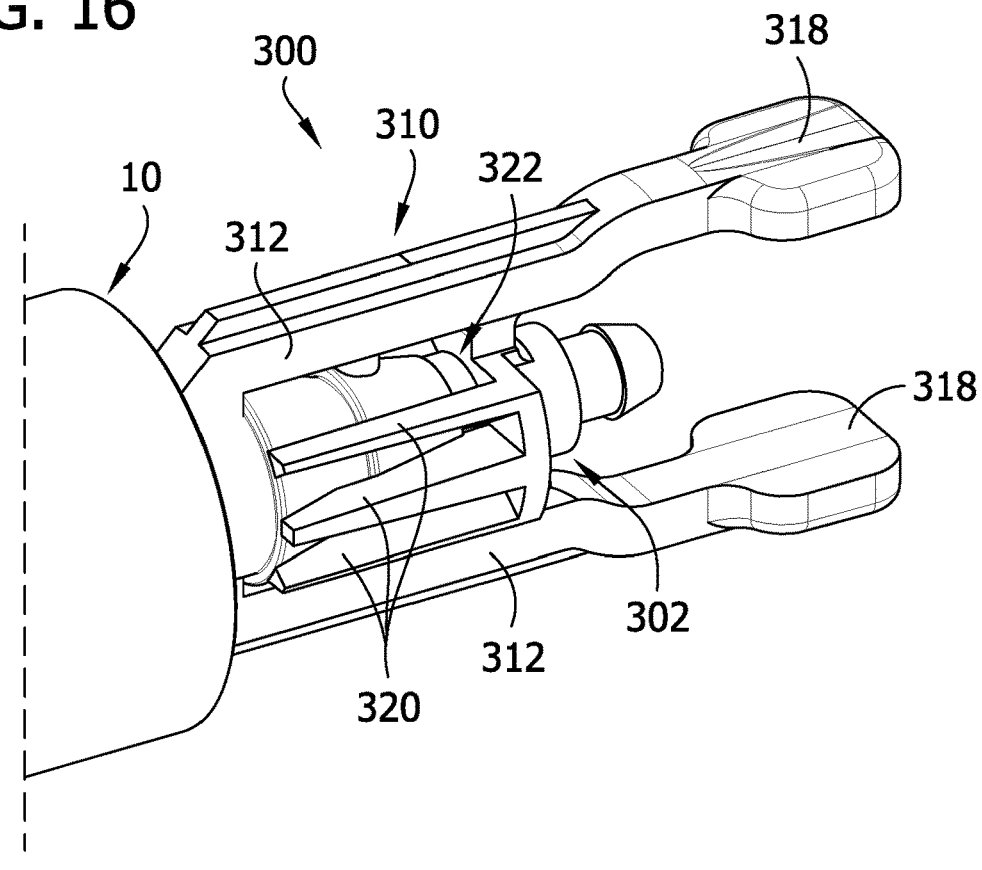
FIG. 16 is a perspective of the port connector of FIG. 16 connected to a fluid port.
FIG. 17 is a longitudinal cross-section thereof.

Referring to FIGS. 15-17, another embodiment of a port connector according to the present disclosure is generally indicate by reference numeral 300. The port connector 300 of FIGS. 15-17 is generally analogous to the port connector 100 of FIGS. 1-6 and thus, for ease of comprehension, where similar, analogous or identical parts are used, reference numerals "200" units higher are employed. Accordingly, unless clearly stated or indicated otherwise, the above descriptions regarding the port connector 100 of FIGS. 1-6 also apply to the port connector 300 of FIGS. 15-17.

In this embodiment, the port connector 300 includes a porous member 322 (broadly, a fluid port interface member). The porous member 322 is supported by the housing 302. In the illustrated embodiment, the porous member 322 is mounted on the insertion portion 303. As shown in FIG. 17, the porous member 322 is arranged relative to the housing 302 to engage the fluid port 10 when the port connector 300 is connected to the fluid port. Specifically, the porous member 322 is arranged to engage the distal end (specifically, the distal end surface 14) of the fluid port 10. The porous member 322 has a porous structure defining a plurality of randomly arranged interconnected interstitial spaces the form a plurality of minute passageways 321 through and/or within the porous member. The porous member 322 is arranged to face and engage the distal end surface 14 of the fluid port 10, when the port connector 300 is attached to the fluid port. The porous member 322 is arranged relative to the housing 302 such that at least a portion of the minute passageways fluidly couple the fluid port outlet 16 to the exterior environment of the port connector 300 when the port connector is connected to the fluid port 10. Accordingly, when the port connector 300 is attached to the fluid port 10, porous member 322 does not form an absolute fluid tight seal with the fluid port. Instead, fluid is able to move through the porous member 322 via the minute passageways 321. However, the port connector 300 may still be considered to form a fluid tight seal (as defined herein) with the fluid port 10, as the porous member 322 sufficiently impedes the flow of fluid therethrough such that fluid flows from other areas (e.g., into the end of the interior lumen(s) of the article opposite the fluid port) as a result of a pressure differential, as explained in more detail below.

The porous member is preferably made of biocompatible, hydrophobic, and/or non-flammable material. In one embodiment, the porous member is made of expanded polyterafluoroethylene (ePTFE), such as FluroFlex® ePTFE, although other suitable materials are within the scope of the present disclosure. In one embodiment, the porous member may have a density within the inclusive range of about 0.3-0.6 g/cm$^3$, or more preferably, within the inclusive range of about 0.4-0.5 g/cm$^3$.

Figure 17A:
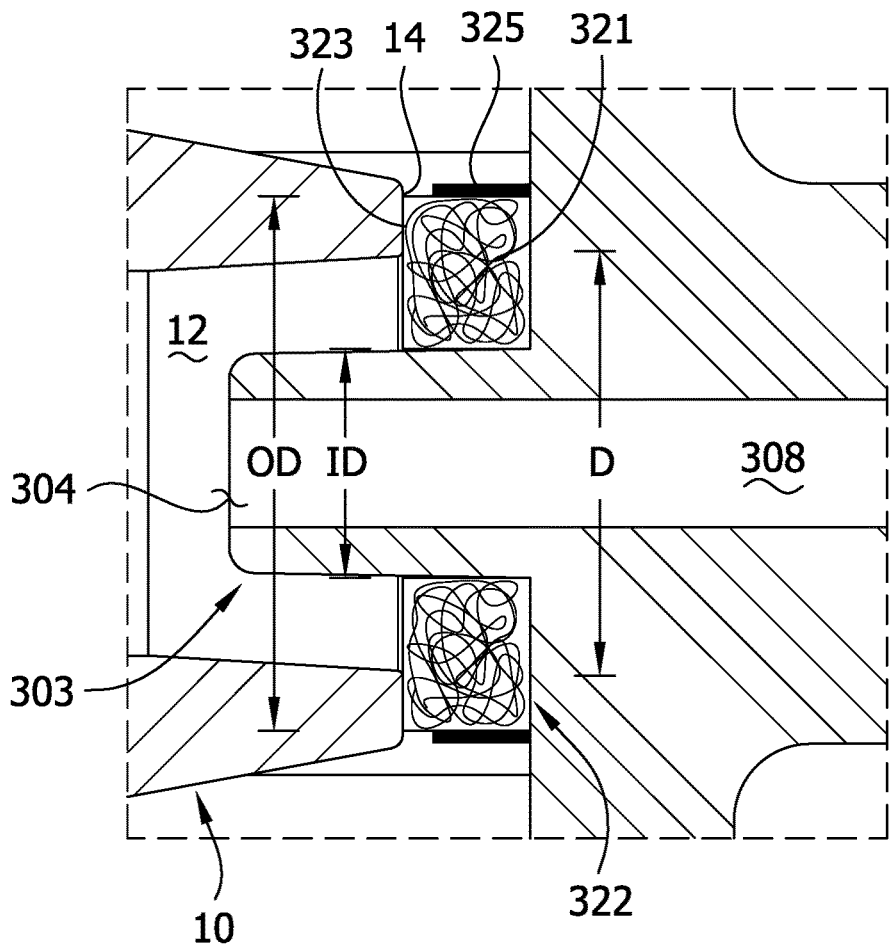
FIG. 17A is an enlarged, fragmentary view of FIG. 17.
Figure 18:
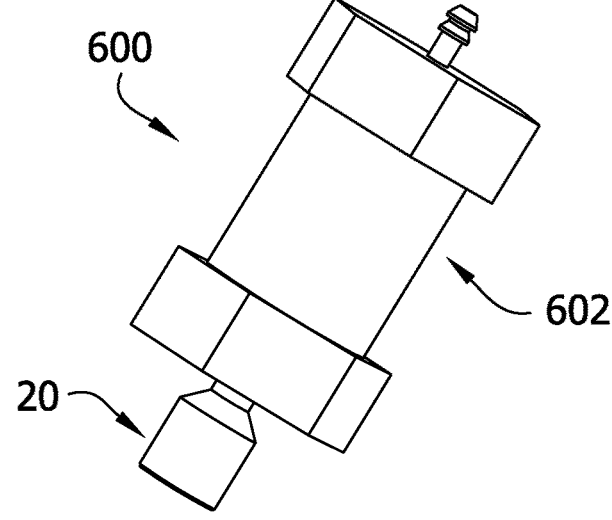
FIG. 18 is a perspective of a port connector according to another embodiment of the present disclosure connected to a fluid port.
Figure 19:
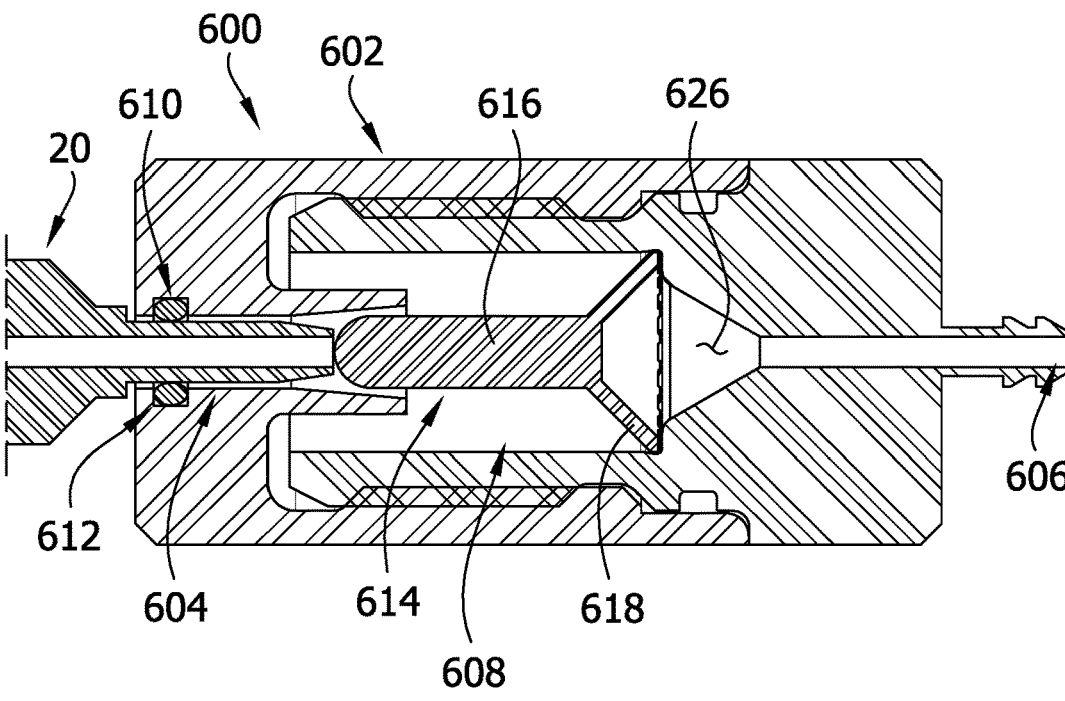
FIG. 19 is a longitudinal cross-section thereof, with the port connector in an initial position on the fluid port.

In one embodiment, as illustrated, the minute passageways 321 of the porous member 322 are generally randomly disposed throughout the entirety of the porous member. In one embodiment, a porous controlling material or coating 325 (FIG. 17A) is applied to the porous member 322. For example, the porous controlling material 325 may be applied to one or more surfaces (e.g., exterior surfaces) of the porous member 322. The porous controlling material 325 may be applied to an entire surface of the porous member 322 or only a portion of the surface. The porous member 322 may be mated or coated with the porous controlling material 325. Applying the porous controlling material 325 to the one or more surfaces of the porous member 322 allows a flow path to be defined through the porous member, instead of relying on the randomness of the minute passageways 321. The porous controlling material 325 at least partially blocks at least a portion of the minute passageways 321 of the porous member 322 to control how and where the sterilization fluid flows through the porous member. The porous controlling material 325 may completely block the minute passageways 321 or only partially block the minute passageways the porous controlling material is aligned with (e.g., covers). The porous controlling material 325 may also increase the resistance to the flow of the sterilization fluid through the porous member 322 to ensure an adequate amount of sterilization fluid is also drawn through the article. Preferably, the resistance to sterilization fluid flow through the article and through the porous member 322 are relatively similar to ensure sterilization fluid is drawn through both the porous member and the article when the pressure differential is applied by the sterilization apparatus. By applying the porous controlling material 325 to the porous member 322, a fluid path through the porous member (via the minute passageways 321) that is closest to or comes into contact with the fluid port 10 (e.g., surfaces thereof) can be more readily defined to better ensure the sterilization fluid comes into contact with the fluid port as the sterilization fluid flows through the porous member. For example, in one embodiment, the porous controlling material 325 is spaced apart from the portion of the porous member that comes into contact with the fluid port 10. The porous controlling material 325 may be non-porous or have a porosity that is less than the porosity of the porous member 322. The porous controlling material 325 may be made of any suitable material, such as polyterafluoroethylene (PTFE).

Still referring to FIG. 17, the porous member 322 is arranged relative to the housing 302 such that the porous member covers a portion (broadly, at least a portion) of the fluid port outlet 16 when the port connector 300 is connected to the fluid port 10. The porous member 322 include an engagement surface 323 arranged to engage the distal end (e.g., distal end surface 14) of the fluid port 10. The engagement surface 323 generally faces proximally. In the illustrated embodiment, the engagement surface 323 has a generally annular shape to match the generally annular end of the fluid port. The engagement surface 323 has an inner diameter ID (FIG. 17A) that is less than a diameter D of the fluid port outlet 16. Likewise, the engagement surface 323 has an outer diameter OD (FIG. 17A) that is greater than the diameter D of the fluid port outlet 16. In one embodiment, the porous member 322 has a generally donut shape.

The porous member 322 permits the sterilization fluid in the environment surrounding the fluid port 10 of the article to come into contact with and sterilize surfaces (e.g., the end surface 14) of the fluid port. When the negative pressure differential is applied via the negative pressure source to the port connector 300, the sterilization fluid moves (e.g., is drawn) through the porous member 322 (specifically, through at least some of the minute passageways 321). Some of these minute passageways 321 lead to and/or along the portion (e.g., end surface 14) of the fluid port 10 the porous member 322 is engaged with. As a result, as the sterilization fluid moves through the porous member 322, the sterilization fluid comes into contact with the fluid port 10, such as the end surface 14, thereby sterilizing the portion of the fluid port engaged by the porous member.

In this embodiment, the housing 302 includes a plurality of port guides 320 configured to engage the fluid port 10 to align the porous member 322 with the end of the fluid port. In the illustrated embodiment, the housing 302 includes six port guides 320, three of which are disposed on one side of the housing and three of which are disposed on the opposite side of the housing. Each port guide 320 comprises a fin or flange that includes an inner edge that engages the fluid port 10 to facilitate positioning of the port connector 300 on the fluid port 10. The inner edge of each port guide 320 is contoured or shaped to match the exterior shape of the fluid port 10. The port guides 320 also act as stops that position (e.g., longitudinally or proximally position) the port connector 300 relative to the fluid port 10.

In operation, to sterilize an article having the fluid port 10, the port connector 300 is connected to the fluid port. As mentioned above, the porous member 322 engages the end (e.g., distal end surface 14) of the fluid port 10. The negative pressure source of the sterilization apparatus is fluidly connected to the port connector 300 (e.g., outlet 306). The article with the fluid port 10 is placed in a chamber (e.g., cleaning chamber). A fluid (e.g., sterilization fluid) is supplied or introduced into the chamber. The fluid may remain in the chamber for a period of time, such as 5-10 minutes, before applying the negative pressure. During this time, the fluid may naturally move or be forcefully moved around the chamber and come into contact with and sterilize surfaces of the article and fluid port, such as exposed surfaces. The fluid may also move into and through the porous member 322. Then, the operator applies the pressure differential (e.g., the negative pressure differential) via the negative pressure source. As a result, the negative pressure differential moves (e.g., draws) the sterilization fluid through the porous member, from the chamber, into the lumen 12 of the fluid port 12. As the sterilization fluid moves through the minute passageways 321 of the porous member 322, the sterilization fluid comes into contact with the distal end surface 14 (and any other surfaces engaged by the porous member), thereby sterilizing the distal end surface of the fluid port 10. In addition, the negative pressure differential moves (e.g., draws) the sterilization fluid into and through the interior lumen(s) of the article and through the fluid port 10 and the port connector 100, thereby sterilizing the interior of the article. The movement of the sterilization fluid through the article and through the porous member 322 occur generally simultaneously. The sterilization fluid drawn through the article and the porous member 322 is then drawn through the port connector 300 and moves toward the negative pressure source. Thus, even though the port connector 300 is attached to the fluid port 10 during the sterilization process, generally the entire fluid port is exposed to the sterilization fluid and sterilized.

Referring to FIGS. 18-23, another embodiment of a port connector according to the present disclosure is generally indicated by reference numeral 600. The port connector 600 is shown attached to a fluid port 20 of an article (not shown), such as an endoscope. Other configurations of the fluid port are within the scope of the present disclosure. The port connector 600 is used for connecting the fluid port 20 of an article or device to be sterilized (via a sterilization fluid) to a pressure source (e.g., a negative pressure source, a positive pressure source, a combination thereof) of a sterilization system or apparatus (not shown), such as the sterilization system described in PCT Publication No. WO 2018/090133. The pressure source creates a pressure differential to move fluid (e.g., a sterilization fluid) from the environment surrounding the article, into interior lumen(s) of the article and through the fluid port 20 and port connector 600 to sterilize the interior surfaces (e.g., interior lumen(s)) of the article. The pressure source can be any suitable pressure source such as a vacuum, a pump, or a chamber having a lower/higher pressure then the environment surrounding the article.

The port connector 600 includes a housing 602. The housing 602 has a proximal end portion and a distal end portion. The proximal end portion defines an inlet 604 configured to be fluidly coupled to the fluid port. The inlet 604 is sized and shaped to receive at least a portion (e.g., a distal portion) of the fluid port 20. In the illustrated embodiment, the inlet 604 is elongate bore. Preferably, the portion of the housing 602 defining the inlet 604 does not engage the fluid port 20. The distal end portion (e.g., distal port) defines an outlet 606 configured to be fluidly coupled to the pressure source. In the illustrated embodiment, the distal end portion is configured to be coupled to a fluid conduit or tube to fluidly couple the outlet 606 to the pressure source. The inlet 604 and the outlet 606 are fluidly coupled to each other. The housing 602 defines a fluid passageway 608 extending between and fluidly coupling the inlet 604 and the outlet 606. The housing 602 is configured to be coupled to the fluid port 20. In the illustrated embodiment, the housing 602 is made up of multiple components secured together. The housing 602 may be made of any suitable material, such as plastic (e.g., polypropylene).

The port connector 600 includes a seal or gasket 610 (broadly, a fluid port interface member). The seal 610 is supported by (e.g., connected to) the housing 602. In particular, the seal 610 is disposed along the inlet 604. The seal 610 is configured to engage the fluid port 20. As explained in more detail below, the seal 610 is configured to move from a first location or position on the fluid port 20 to a second location or positon on the fluid port. The seal 610 engages the fluid port 20 to inhibit the flow of fluid between the seal and the fluid port. Preferably, the seal 610 forms an absolute fluid tight seal with the fluid port 20. In the illustrated embodiment, the seal 610 is an O-ring. The housing 602 includes a groove 612 (e.g., circumferential groove) in which the seal 610 is disposed. The seal 610 extends inward (e.g., radially inward) from the interior surface defining the inlet 610 to engage the fluid port 20. The seal 610 can be made of any suitable material such as a thermoplastic elastomer (TPE) (e.g., styrene-ethylene-buty-lene-styrene (SEBS)).

The port connector 600 includes a piston or plunger 614. The plunger 614 is movably (e.g., slidably) disposed within the housing 602. The plunger 614 is disposed in the fluid passageway 608. The plunger 614 includes a flange 618 and a shaft 616 extending proximally from the flange. The flange 618 has a generally conical shape. The flange 618 tapers outward (e.g., radially outward) as the flange extends distally from the shaft 616. The outer edge of the flange 618 (broadly, the plunger 614) includes one or more slots 620. The slots 620 are configured to permit the flow of fluid around the plunger 614. As explained in more detail below, the slots 620 permit the fluid the flow from the inlet 604 to the outlet 606. The plunger 614 can be made of any suitable material, such as plastic (e.g., polyethylene, polypropylene, polytetrafluoroethylene).

Figure 20:
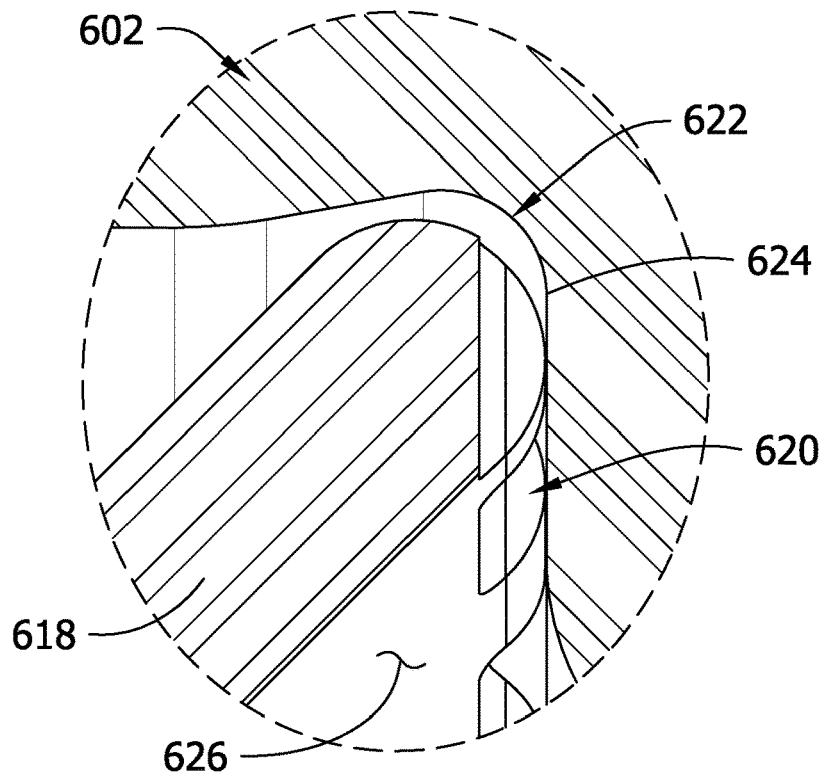
FIG. 20 is an enlarged, fragmentary view of FIG. 19.
Figure 21:
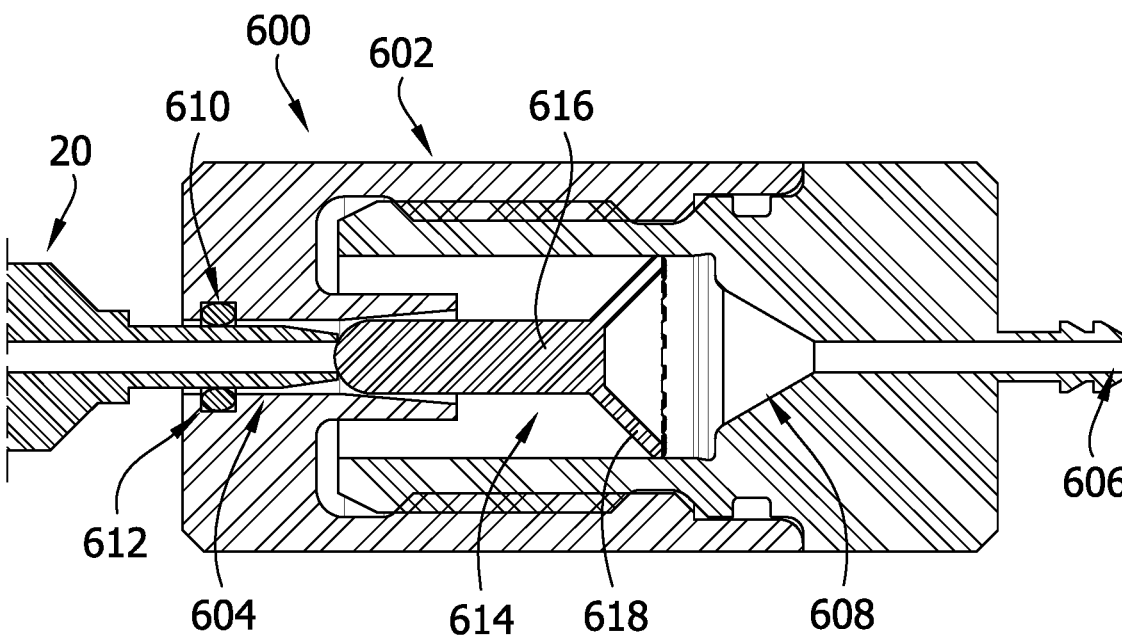
FIG. 21 is a longitudinal cross-section of FIG. 18, with the port connector in a second position on the fluid port.
Figure 22:
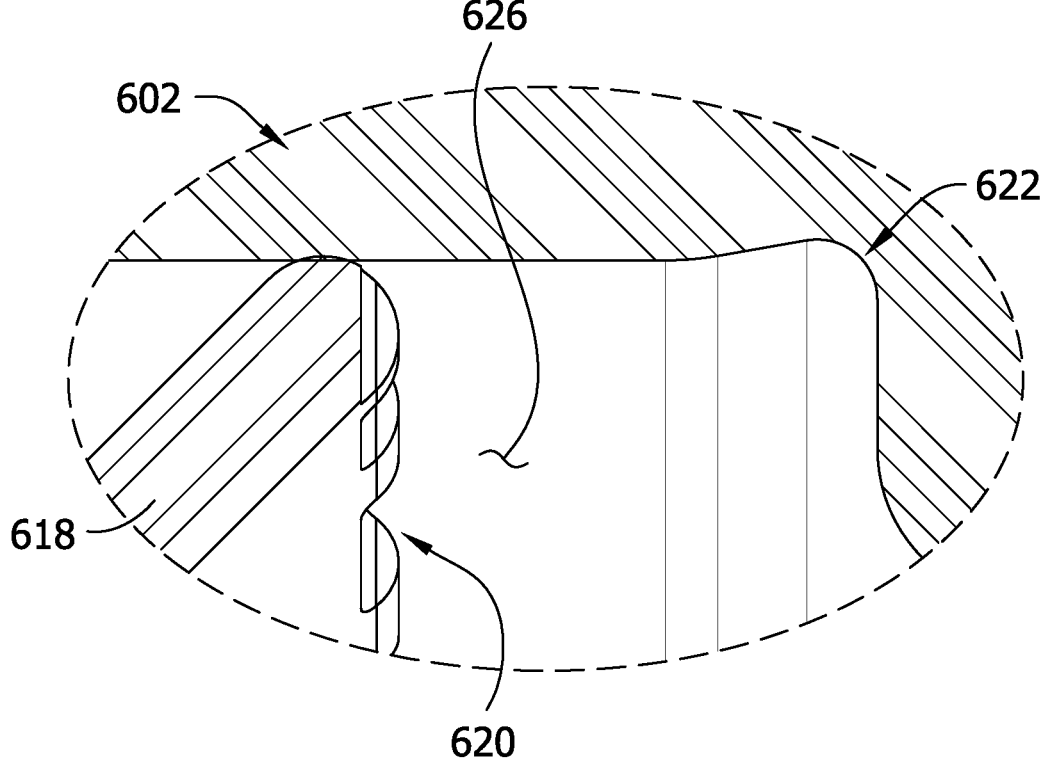
FIG. 22 is an enlarged, fragmentary view of FIG. 21.
Figure 23:
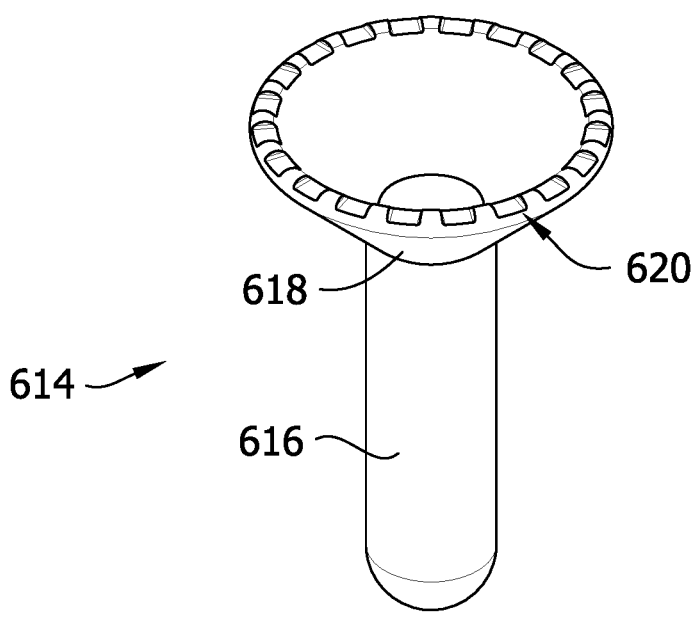
FIG. 23 is a perspective of a plunger of the port connector of FIG. 18.

The plunger 614 is configured to move from an initial position (FIGS. 19 and 20) to a second position (FIGS. 21 and 22) within the housing 602. The plunger 614 moves proximally or toward the fluid port from the initial position to the second position (and distally from the second position to the initial position). In the initial position, the plunger 614 (and housing 602) is configured to permit the fluid to flow between the inlet 604 and the outlet 606. As shown in FIG. 20, the housing 602 defines a plunger recess 622. When the plunger 614 is in the initial position, the outer edge of the flange 618 is aligned (e.g., laterally aligned) with the plunger recess 622. In some embodiments, the plunger recess 622 may be sized and shaped to receive the outer edge of the flange 618. The plunger recess 622 provides clearance between outer edge of the flange 618 and an interior surface of the housing 602 to permit the fluid to flow around the plunger (e.g., flange) via the plunger recess 622 and the slot 620 toward the outlet 606. In the illustrated embodiment, the flange 618 engages a distal interior surface 624 of the housing 602 when the plunger is in the initial position. The distal interior surface 624 acts as a stop that limits the distal movement of the plunger 614 relative to the housing 602 and positions the plunger in the initial position. In the initial position, the plunger 614 is preferably spaced apart from the fluid port 20. In the second position, and as the plunger moves proximally toward the second position, the outer edge of the flange 618 engages the interior surface of the housing 602. This engagement forms the seal between the plunger 614 and the housing 602 to prevent or inhibit the flow of fluid between the plunger and the housing.

The fluid passageway 608 includes a fluid chamber 626. The fluid chamber is defined by the plunger 614 (e.g., flange 618) and the housing 602. As will be explained in more detail below, the fluid chamber 626 is configured to expand or increase in volume due to the application of positive pressure (i.e., positive pressure differential) from the pressure source (when the plunger 614 is in the initial position). The fluid chamber 626 is also configured to generally collapse or reduce in volume due to the application of negative pressure (i.e., negative pressure differential) from the pressure source (when the plunger 614 is in the second position). As used herein, the phrase "positive pressure" means a pressure that is higher than a pressure of the environment surrounding the relative component(s) to which the positive pressure is being applied, such as the port connector 600. For example, applying positive pressure from a pressure source to the port connector 600 means the pressure source imparts a higher pressure on the port connector relative to the pressure in the environment surrounding the port connector (e.g., the chamber of the sterilization system in which the port connector is positioned). In other words, the positive pressure creates a positive pressure differential between the environment surrounding the relative components and the pressure source, thereby causing fluid to flow from the pressure source toward the environment. A positive pressure can be a pressure at or above atmospheric pressure or a pressure below atmospheric pressure (vacuum). In certain preferred embodiments, a positive pressure is at or above atmospheric pressure.

The plunger 614 is configured to push against the fluid port upon the application of the positive pressure from the pressure source to move the housing 602 and the seal 610 distally relative to the fluid port 20, thereby moving the seal to a second location or position on the fluid port. Specifically, the plunger 614 moves proximally relative to the housing 602 due to the application of the pressure differential (i.e., positive pressure) to expand the fluid chamber 626 and push against the fluid port 20. Thus, the plunger 614 engages the fluid port 20 as the plunger moves from the initial position to the second position. The plunger 614 generally forms a seal (e.g., a fluid tight seal) with the housing 602 as the plunger moves proximally from the initial position to upon the application of the positive pressure from the pressure source to inhibit the flow of fluid between the inlet 604 and the outlet 606. The plunger recess 622 and the slots 620 provide a sufficient constriction to the flow of fluid such that upon the application of the positive pressure, the positive pressure will move the plunger proximally such that the flange 618 engages the inner surface of the housing.

Moving the seal 610 on the fluid port 20 by moving the plunger 614 exposes the portion of the fluid port at the first location (that was otherwise blocked or covered by the seal 610 when the port connector 600 was initially coupled to the fluid port) to the fluid in the environment surrounding the fluid port of the article to come into contact with and sterilize the portion of the surface at the first location. It is appreciated that the portion of the surface at the second location was previously sterilized by the fluid when the fluid was initially drawn through the port connector 600, as described below. The plunger 614 is also configured to move distally toward the initial position after the plunger pushes against the fluid port 20 to reduce in volume (e.g., collapse, contract) the fluid chamber 626 upon the application of negative pressure from the pressure source.

In the illustrated embodiment, a distally portion of the inlet 604 is tapered (e.g., tapers radially inward as the inlet extends proximally). The plunger 614 (e.g., tip of the shaft 616) is sized and shaped to move along the inlet 604. The taper of the inlet 604 helps guide the plunger 614 into engagement with the fluid port 20. In addition, preferably the taper of the inlet 604 reduces the size of the inlet such that as the plunger moves proximally, the plunger will eventually engage a portion of the housing 602 defining the inlet, thereby stopping further movement. Thus, this portion of the housing 602 acts as a stop to limit the proximal movement of the plunger 614 and position the plunger in the second position.

In operation, to sterilize an article having the fluid port 20, the port connector 600 is connected to the fluid port. When connected, the seal 610 engages the fluid port 20 at the first location. The pressure source is fluidly connected to the port connector 600 (e.g., outlet 606). The article with the fluid port 20 is placed in a chamber (e.g., cleaning chamber). A fluid (e.g., sterilization fluid) is supplied or introduced into the chamber. The fluid may remain in the chamber for a period of time, such as 5-10 minutes, before applying negative pressure. During this time, the fluid may naturally move or be forcefully moved around the chamber and come into contact with and sterilize surfaces of the article and fluid port. Then, the operator applies the negative pressure via the pressure source. The application of negative pressure moves (e.g., draws) fluid into the interior lumen(s) of the article and through the fluid port 20 and port connector 600, thereby sterilizing the interior of the article. The fluid flows from the inlet 604, around the plunger 614 via the plunger recess 622 and slots 620 and into the outlet 606. As the fluid flows into the inlet 604, the fluid flows over the second location on the fluid port 20. After a sufficient amount of fluid has been drawn through the article, the operator can apply a positive pressure via the pressure source. As a result of the application of positive pressure, the seal 610 is moved along the fluid port 20 from the first location to the second location. As described above, the application of positive pressure moves the plunger 614 relative to the housing 602 to move the seal 610. Specifically, the application of the positive pressure expands the fluid chamber 626, pushing the plunger into contact with the fluid port 20. Once the plunger 614 contacts the fluid port 20, the continued application of positive pressure continues to expand the fluid chamber 626 by moving the housing 602 (and therefore the seal 610) distally relative to the plunger (which is now prevent from any further proximal movement due to its engagement with the fluid port). In one method of operation, the movement of the plunger 614 disconnects or disengages the port connector 600 (e.g., the seal 610) from the fluid port 20. Specifically, not only does the plunger 614 move the seal 610 to the second location, it continues to move the seal until the seal is no longer engaged with the fluid port 20 such as by sliding the seal off the distal end of the fluid port. In another method of operation, after the application of positive pressure, the operator may then reapply a negative pressure via the pressure source, which moves the plunger 614 distally, back to the initial position. The reapplication of negative pressure creates a vacuum in the fluid chamber 626 which moves the plunger 614 distally relative to the housing 602 into the initial position. Once in the initial position, the fluid is free to flow around the plunger 614 again.

Figure 24:
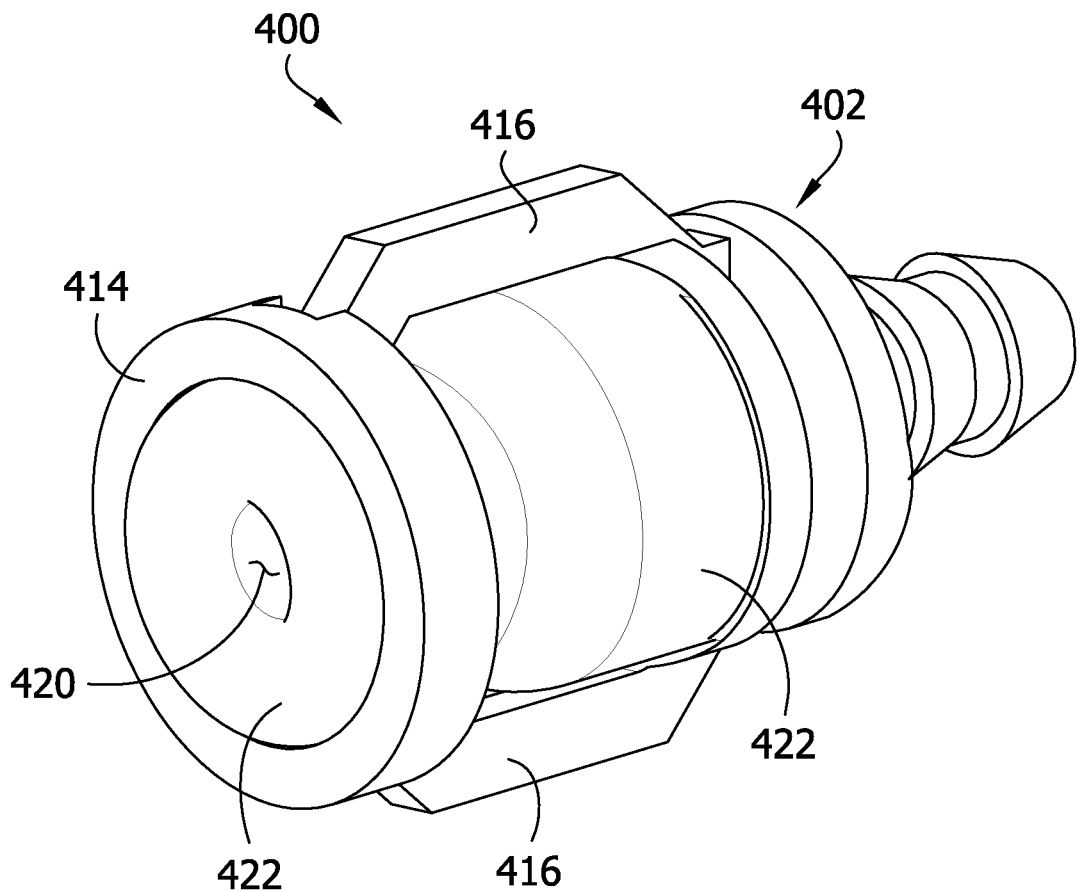
FIG. 24 is a perspective of a port connector according to another embodiment of the present disclosure.
Figure 25:
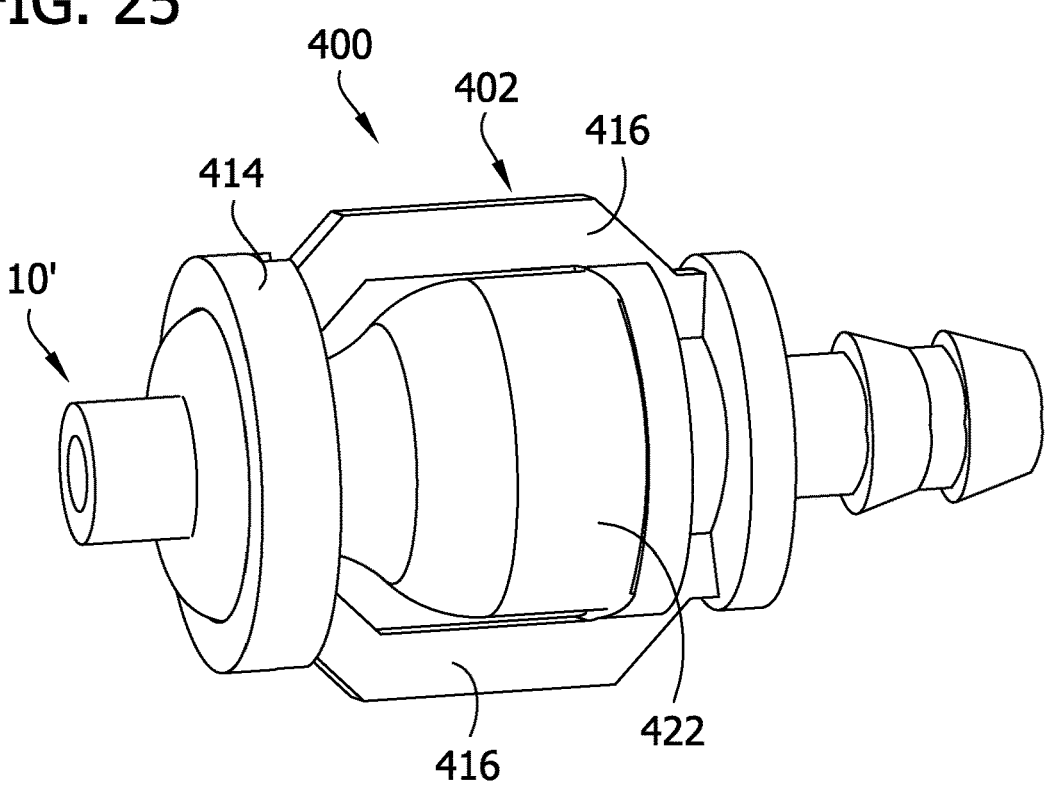
FIG. 25 is a perspective of the port connector of FIG. 24 connected to a fluid port.
Figure 26:
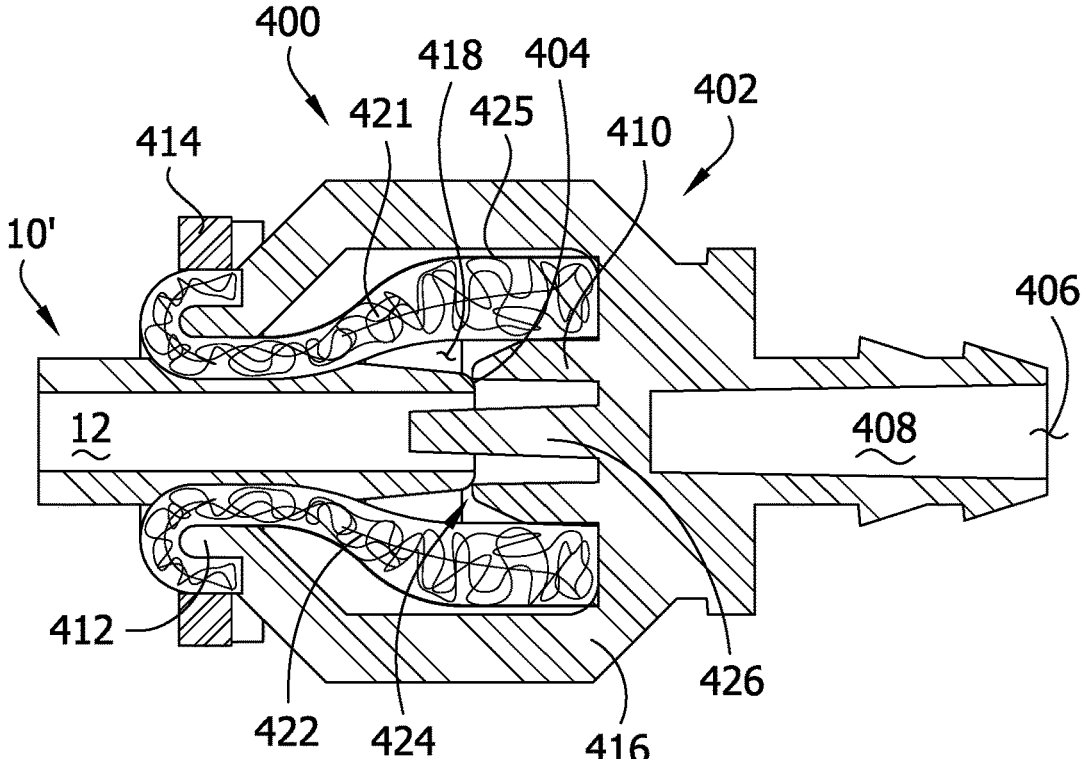
FIG. 26 is a longitudinal cross-section of FIG. 25.

Referring to FIGS. 24-27, another embodiment of a port connector according to the present disclosure is generally indicated by reference numeral 400. As shown in FIGS. 25 and 26, the port connector 400 attaches to fluid port 10' of an article (not shown), such as an endoscope, to be sterilized. The fluid port 10' shown in FIGS. 25 and 26 is generally the same as the fluid port 10 described above except that the fluid port 10' does not have any barbs on its exterior. Instead, the fluid port 10' has a generally smooth, cylindrical exterior surface.

The port connector 400 includes a housing 402. The housing 402 has a proximal end portion and a distal end portion. The distal end portion (e.g., distal port) defines an outlet 406 configured to be fluidly coupled to the negative pressure source (broadly, the sterilization apparatus). In other words, the outlet 406 is arranged to be in fluid communication with the negative pressure source. In the illustrated embodiment, the distal end portion is configured to be coupled to a fluid conduit or tube to fluidly couple the outlet 406 to the negative pressure source. The distal end portion comprises a barbed tube port fitting. The housing 406 also defines an inlet 404 configured to be fluidly coupled to the fluid port 10', specifically the lumen 12 thereof. In other words, the inlet 404 is arranged to be in fluid communication with the fluid port 10', specifically the lumen 12 thereof. The housing 402 defines a fluid passageway 408 (e.g., lumen, bore) extending between and fluidly coupling (e.g., providing fluid communication between) the inlet 404 and the outlet 406.

In this embodiment, the port connector 400 includes a porous member 422 (broadly, a fluid port interface member). The porous member 422 is coupled to the housing 402. In the illustrated embodiment, the porous member 422 is mounted on the housing 402. The porous member 422 is a flexible, deformable and has a generally tubular shape. The housing 402 includes a cylindrical wall 410. The porous member 422 has a proximal end portion and a distal end portion, both being coupled to the housing 402. The distal end portion of the porous member 422 is mounted on the cylindrical wall 410 (e.g., the cylindrical wall is disposed in the porous member). The cylindrical wall 410 defines a portion of the fluid passageway 408. The housing 402 also includes a mounting ring 412. The mounting ring 412 is disposed proximally of the cylindrical wall 410 and the inlet 404. The proximal end portion of the porous member 422 is mounted on the mounting ring 412. The connector 400 include a retaining ring 414 (broadly, a retainer) that secures the porous member 422 (the proximal end portion thereof) to the mounting ring 412. In the illustrated embodiment, the porous member 422 doubles back on itself to be secured to the mounting ring 412. The proximal end portion of the porous member 422 bends around the mounting ring 412. The retaining ring 414 then clamps or secures the proximal end portion of the porous member 422 against the exterior of the mounting ring 412. The housing 402 includes one or more supports 416 to the support the mounting ring 412. The supports 416 extend between and couple the mounting ring 412 to the main body of the housing 422.

The connector 400 defines a receiving chamber 418. The receiving chamber 418 is sized and shaped to receive the fluid port 10'. The porous member 422 defines at least a portion of the receiving chamber 418. The inlet 404 of the housing 402 is in fluid communication with the receiving chamber 418. The inlet 404 is disposed in the portion of the receiving chamber 418 defined by the porous member 422. In the illustrated embodiment, the inlet 404 is disposed generally adjacent the distal end of the receiving chamber 418. The receiving chamber 418 includes a port or receiving inlet 420 (FIG. 24). The port inlet 420 is sized and shaped to receive the fluid port 10' to permit the fluid port to be inserted into the receiving chamber 418. The port inlet 420 is disposed at the proximal end of the receiving chamber. In the illustrated embodiment, the port inlet 420 is defined by the porous member 422. The porous member 422 defines the proximal end of the port connector 400.

As shown in FIGS. 25 and 26, the porous member 422 is arranged to engage the fluid port 10' when the port connector 400 is connected to the fluid port. Specifically, the porous member 422 (specifically, an interior or engagement surface thereof) is arranged to engage the fluid port 10' when the fluid port is disposed in the receiving chamber 418. The porous member 422 is arranged to engage the cylindrical exterior surface of the fluid port 10'. Preferably, the porous member 422 is configured to form an interference or friction fit with the fluid port 10'. The porous member 422 has an inner diameter at the narrowest point of the receiving chamber 418 (when the porous member is at rest and undeflected by the fluid port 10'). The inner diameter is equal to, or more preferably, less than an outer diameter of the fluid port 10'. This ensures the porous member 422 will engage and be deformed by the fluid port 10', with the resilient deformation applying a force against the fluid port to hold the port connector 400 thereon. In other words, the porous member squeezes against the fluid port. FIG. 26 shows the porous member 422 in its at rest, undeformed state, however it is understood that the fluid port 10' would deform the porous member, by expanding the port inlet 420 and/or receiving chamber 418 (e.g., a portion of the receiving chamber) to permit the fluid port to be received in the port connector 400.

The porous member 422 has a porous structure defining a plurality of randomly arranged interconnected interstitial spaces that form a plurality of minute passageways 421 through and/or within the porous member. The porous member 422 is arranged relative to the rest of the port connector 400 such that at least a portion of the minute passageways 421 fluidly couple the receiving chamber 418 to the exterior environment of the port connector 400. Accordingly, when the port connector 400 is attached to the fluid port 10', porous member 422 does not form an absolute fluid tight seal with the fluid port. Instead, fluid is able to move through the porous member 422 via the minute passageways. However, the port connector 400 may still be considered to form a fluid tight seal (as defined herein) with the fluid port 10', as the porous member 422 sufficiently impedes the flow of fluid therethrough such that fluid flows from other areas (e.g., into the end of the interior lumen(s) of the article opposite the fluid port) as a result of a pressure differential, as explained in more detail below. The porous member 422 may be made of the same material as described above in relation to porous member 322.

The porous member 422 permits the sterilization fluid in the environment surrounding the fluid port 10' of the article to come into contact with and sterilize surfaces (e.g., the end surface 14, the cylindrical exterior surface) of the fluid port. When the negative pressure differential is applied via the negative pressure source to the port connector 400, the sterilization fluid moves (e.g., is drawn) through the porous member 422 (specifically, through at least some of the minute passageways 421). Some of these minute passageways 421 lead to and/or along the portion of the fluid port 10' the porous member 422 is engaged with. As a result, as the sterilization fluid moves through the porous member 422, the sterilization fluid comes into contact with the fluid port 10', thereby sterilizing the portion of the fluid port engaged by the porous member.

In one embodiment, as illustrated, the minute passageways 421 of the porous member 422 are generally randomly disposed throughout the entirety of the porous member. In one embodiment, a porous controlling material or coating

425 (FIG. 26) is applied to the porous member 422. For example, the porous controlling material 425 may be applied to one or more surfaces (e.g., exterior surfaces) of the porous member 422. The porous controlling material 425 may be applied to an entire surface of the porous member 422 or only a portion of the surface. The porous member 422 may be mated or coated with the porous controlling material 425. Applying the porous controlling material 425 to the one or more surfaces of the porous member 422 allows a flow path to be defined through the porous member, instead of relying on the randomness of the minute passageways 421. The porous controlling material 425 at least partially blocks at least a portion of the minute passageways 421 of the porous member 422 to control how and where the sterilization fluid flows through the porous member. The porous controlling material 425 may completely block the minute passageways 421 or only partially block the minute passageways the porous controlling material is aligned with (e.g., covers). The porous controlling material 425 may also increase the resistance to the flow of the sterilization fluid through the porous member 422 to ensure an adequate amount of sterilization fluid is also drawn through the article. Preferably, the resistance to sterilization fluid flow through the article and through the porous member 422 are relatively similar to ensure sterilization fluid is drawn through both the porous member and the article when the pressure differential is applied by the sterilization apparatus. By applying the porous controlling material 425 to the porous member 422, a fluid path through the porous member (via the minute passageways 421) that is closest to or comes into contact with the fluid port 10' (e.g., surfaces thereof) can be more readily defined to better ensure the sterilization fluid comes into contact with the fluid port as the sterilization fluid flows through the porous member. For example, in one embodiment, the porous controlling material 425 is disposed distally the proximal end portion of the porous member 422 so that a fluid path is defined that flows into the proximal end portion of the porous member, along the exterior surface of the port 10' and into the receiving chamber 418. The porous controlling material 425 may be non-porous or have a porosity that is less than the porosity of the porous member 422. The porous controlling material 425 may be made of any suitable material, such as polyterafluoroethylene (PTFE).

Figure 27:
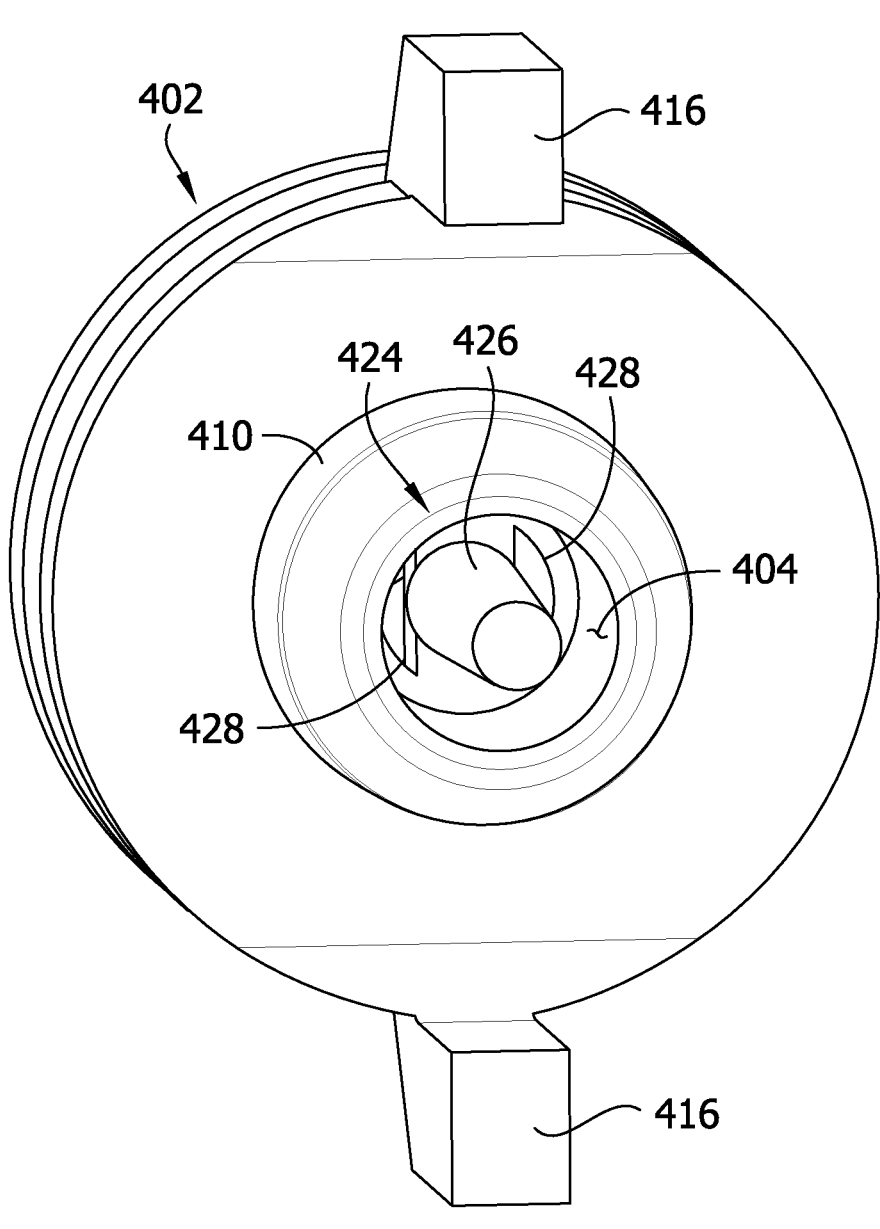
FIG. 27 is a lateral cross-section of FIG. 24, with a porous member removed to reveal interior details.

Referring to FIGS. 26 and 27, the housing 402 includes a stop 424. The stop 424 is arranged to engage the fluid port 10' to position the fluid port in the receiving chamber 418. The stop 424 is arranged to engage the distal end 14 of the fluid port 10'. The stop 424 limits the distal movement of the fluid port 10' relative to the port connector 400 in the insertion direction. The insertion direction being the direction in which the fluid port 10' moves relative to the port connector 400 when the port connector is connected to the fluid port—i.e., the direction the fluid connector is inserted into the port inlet 420. In the illustrated embodiment, the stop 424 includes an edge arranged to engage the fluid port 10. The edge is disposed at the proximal end of the cylindrical wall 410. Preferably, the stop 424 is the only portion of the housing 402 arranged to engage the fluid port 10', to prevent the housing from otherwise interfering with the flow of the sterilization fluid around the fluid port 10'. Preferably, the stop 424 permits the sterilization fluid to flow between it and the fluid port 10' when the stop is engaged with the fluid port and the pressure differential is applied. As such, the narrow edgewise engagement of the stop 424 disclosed herein does not form a seal with the fluid port 10', thereby permitting the sterilization fluid to flow between the stop and the fluid port. In one embodiment, the stop 424 may define recesses or channels (not shown) to further facilitate the flow of the sterilization fluid between the stop and the fluid port 10'. In the illustrated embodiment, the stop 424 defines the inlet 404.

The port connector 400 may include a port guide 426. The port guide 426 is configured to generally align the lumen 12 of the fluid port 10' with the inlet 404. The port guide 426 is sized and shaped to be received in the lumen 12 of the fluid port 10'. In the illustrated embodiment, a portion of the port guide 426 is disposed in the fluid passageway 408. The port guide 426 is mounted to an interior wall of the housing 402 (broadly, the port guide is part of the housing). The interior wall defines one or more openings 428 (FIG. 27) which are part of the fluid passageway 408 and permit the sterilization fluid to flow therethrough as the sterilization fluid flows from the inlet 404 to the outlet 406. The port guide 426 extends proximally from the interior wall of the housing 402. The port guide 426 extends through the inlet 404. In the illustrated embodiment, the port guide 426 has a generally truncated conical shape, although other shapes are within the scope of the present disclosure. The port guide 426 ensures the fluid port 10' will be properly positioned relative to the port connector 400 when the port connector is mounted on the fluid port.

In operation, to sterilize an article having the fluid port 10', the port connector 400 is connected to the fluid port by inserting the fluid port through the port inlet 420 and into the receiving chamber 418. As mentioned above, the porous member 422 engages the fluid port 10'. The negative pressure source of the sterilization apparatus is fluidly connected to the port connector 400 (e.g., outlet 406). The article with the fluid port 10' is placed in a chamber (e.g., cleaning chamber). A fluid (e.g., sterilization fluid) is supplied or introduced into the chamber. The fluid may remain in the chamber for a period of time, such as 5-10 minutes, before applying the negative pressure. During this time, the fluid may naturally move or be forcefully moved around the chamber and come into contact with and sterilize surfaces of the article and fluid port, such as exposed surfaces. The fluid may also move into and through the porous member 422. Then, the operator applies the pressure differential (e.g., the negative pressure differential) via the negative pressure source. As a result, the negative pressure differential moves (e.g., draws) the sterilization fluid through the porous member, from the chamber, into the receiving chamber 418. As the sterilization fluid moves through some of the minute passageways 421 of the porous member 422, the sterilization fluid comes into contact with the cylindrical exterior surface, thereby sterilizing the portion of the fluid port 10' engaged by the port connector. After the sterilization fluid enters the receiving chamber 418, the sterilization fluid also moves around the fluid port 10', sterilizing the rest of the fluid port received in the receiving chamber before the sterilization fluid enters the inlet 404 of the port connector 400. It is believed aligning (e.g., laterally aligning) the inlet 404 with the porous member 422 results in a more substantial flow of the sterilization fluid through the porous member. In addition, the negative pressure differential moves (e.g., draws) the sterilization fluid into and through the interior lumen(s) of the article and through the fluid port 10' and the port connector 400, thereby sterilizing the interior of the article. The movement of the sterilization fluid through the article and through the porous member 422 occurs generally simultaneously. The sterilization fluid drawn through the article and the porous member 422 is then drawn through the port connector 400 and moves toward the negative pressure source. Thus, even though the port connector 400 is attached to the fluid port 10' during the sterilization process, generally the entire fluid port is exposed to the sterilization fluid and sterilized.

OTHER STATEMENTS OF THE DISCLOSURE

The following are statements of example embodiments described in the present disclosure. Although some of the following statements are not currently presented as claims, the statements are believed to be patentable and may subsequently be presented as claims. Associated methods corresponding to the statements or apparatuses or systems below, are also believed to be patentable and may subsequently be presented as claims. Likewise, associated apparatuses or systems corresponding to the statements or methods below, are also believed to be patentable and may subsequently be presented as claims. It is understood that the following statements may refer to and be supported by one, more than one or all of the embodiments described above.

A1. A port connector for connecting to a fluid port of a device to be sterilized to a negative pressure source of a sterilization apparatus, the port connector comprising: a housing configured to couple to the fluid port, the housing having a proximal end portion defining an inlet configured to be fluidly coupled to the fluid port and a distal end portion defining an outlet configured to be fluidly coupled to the negative pressure source, the housing defining a fluid passageway extending between and fluidly coupling the inlet and outlet; and a gasket supported by the housing such that the gasket is spaced apart from the fluid port when the housing is coupled to the fluid port, the gasket configured to move toward and engage the fluid port to form a fluid tight seal with the fluid port upon the application of negative pressure from the negative pressure source in order to draw fluid through the fluid port.

A2. The port connector of statement A1, wherein the proximal end portion includes an insertion portion sized and shaped to be inserted into the fluid port, the insertion portion defining the inlet.

A3. The port connector of any one of statements A1-A2, wherein the gasket includes a bendable flange, the bendable flange configured to move toward and engage the fluid port to form the fluid tight seal with the fluid port due to the application of negative pressure.

A4. The port connector of any one of statements A1-A2, wherein the housing includes a plunger supporting the gasket, the plunger configured to move proximally upon the application of negative pressure to move the gasket toward the fluid port so that the gasket engages the fluid port to form the fluid tight seal with the fluid port.

A5. The port connector of statement A4, wherein the fluid passageway defined by the housing includes a fluid chamber, the fluid chamber configured to generally collapse due to the application of negative pressure.

A6. The port connector of statement A5, wherein the housing includes a connector body and a slide movably supported by the connector body, the slide being operatively coupled to the plunger such that movement of the slide results in movement of the plunger.

A7. The port connector of statement A6, wherein the connector body and the slide at least partially define the fluid chamber, wherein the slide moves proximally relative to the connector body due to the application of negative pressure to generally collapse the fluid chamber and move the plunger proximally to move the gasket toward the fluid port so that the gasket engages the fluid port to form the fluid tight seal with the fluid port.

A8. The port connector of statement A7, wherein the plunger defines the inlet, the plunger further defining at least one plunger opening in fluid communication with the fluid chamber and an elongate bore fluidly coupling the inlet and at least one plunger opening.

A9. The port connector of any one of statements A7-A8, wherein the slide defines at least one slide passageway fluidly coupling the fluid chamber to the outlet.

A10. The port connector of any one of statements A1-A9, wherein the housing includes a coupler configured to couple to the fluid port.

A11. The port connector of statement A10, wherein the coupler comprises a first resiliently deflectable clip and a second resiliently deflectable clip, the first and second clips configured to engage the fluid port to couple the port connector to the fluid port.

A12. The port connector of statement A11, wherein first and second clips each includes retainer configured to engage the fluid port to secure the port connector to the fluid port.

B1. A method of sterilizing a device having a fluid port, the method comprising: connecting a port connector to the fluid port, the port connector having an inlet in fluid communication with the fluid port, an outlet and a fluid passageway extending between the fluidly connecting the inlet and outlet; fluidly connecting a negative pressure source to the outlet of the port connector; forming a fluid tight seal between the port connector and the fluid port by moving a gasket of the port connector toward and into engagement with the fluid port; and moving a sterilization fluid through the fluid port and port connector.

B2. The method of statement B2, further comprising placing the device in a cleaning chamber and supplying the sterilization fluid to the cleaning chamber before the moving of the sterilization fluid.

B3. The method of any one of statements B1-B2, wherein the gasket includes a bendable flange and wherein the fluid tight seal is formed by bending the bendable flange to move the bendable flange toward and into engagement with the fluid port.

B4. The method of any one of statements B1-B2, wherein the port connector includes a plunger supporting the gasket, and wherein said forming the fluid tight seal includes moving the plunger to move the gasket toward and into engagement with the fluid port.

B5. The method of statement B4, wherein the port connector includes a connector body and a slide moveably supported by the connector body, the slide operatively connected to the plunger such that movement of the slide results in movement of the plunger, and wherein said forming the fluid tight seal includes moving the slide relative to the connector body to move the plunger and thereby the gasket toward and into engagement with the fluid port.

B6. The method of statement B5, wherein the connector body and the slide at least partially define a fluid chamber of the fluid passageway, wherein said forming the fluid tight seal includes creating a vacuum in the fluid chamber thereby moving the slide relative to the connector body to generally collapse the fluid chamber as a result of the vacuum.

B7. The method of any one of statements B1-B6, wherein the gasket is spaced apart from the fluid port before said forming the fluid tight seal.

B8. The method of any one of statements B1-B7, wherein the port connector includes a coupler to connect the port connector to the fluid port.

B9. The method of any one of statements B1-B8, wherein said forming the fluid tight seal includes applying negative pressure to the port connector via the negative pressure source.

B10. The method of any one of statements B1-B9, wherein said moving the sterilization fluid includes drawing the sterilization fluid through the fluid port and port connector via application of negative pressure from the negative pressure source.

C1. A port connector for connecting to a fluid port of a device to be sterilized to a pressure source of a sterilization apparatus, the port connector comprising: a housing configured to couple to the fluid port, the housing having a proximal end portion defining an inlet configured to be fluidly coupled to the fluid port and a distal end portion defining an outlet configured to be fluidly coupled to the pressure source, the inlet being fluidly coupled to the outlet; a seal supported by the housing and configured to engage the fluid port at a first location; and a piston movably disposed within the housing, the piston configured to push against the fluid port upon application of a positive pressure from the pressure source to move the housing and seal distally relative to the fluid port to move the seal to a second location on the fluid port.

C2. The port connector of statement C1, wherein at least the piston and the housing define a fluid chamber, fluid chamber configured to expand due to the application of positive pressure.

C3. The port connector of statement C2, wherein the piston moves proximally relative to the housing due to the application of positive pressure to expand the fluid chamber and push against the fluid port.

C4. The port connector of any one of statements C1-C3, wherein the piston is movable from an initial position, wherein in the initial position the piston is configured to permit fluid to flow between the inlet and the outlet.

C5. The port connector of statement C5, wherein the piston is configured to move proximally from the initial position to push against the fluid port, wherein the piston generally forms a fluid tight seal with the housing when the piston is moved proximally upon the application of positive pressure to inhibit the flow of fluid between the outlet and inlet.

C6. The port connector of any one of statements C1-05, wherein the piston includes one or more slots configured to permit the flow of fluid around the piston.

C7. The port connector of any one of statements C4-05, wherein the piston is configured to move distally toward the initial position after the piston pushes against the fluid port to contract the fluid chamber upon the application of a negative pressure from the pressure source D1. A method of sterilizing a device having a fluid port, the method comprising: connecting a port connector to the fluid port such that a seal of the port connector engages the fluid port at a first location; fluidly connecting a pressure source to an outlet of the port connector; and moving a piston of the port connector relative to a housing of the port connector via application of pressure from the pressure source to move the seal to a second location on the fluid port.

D2. The method of statement D1, wherein moving the piston includes applying positive pressure from the pressure source.

E1. A port connector for connecting to a fluid port of a device to be sterilized to a sterilization apparatus, the fluid port defining a lumen, the port connector comprising: a porous member having a porous structure defining a plurality of minute passageways, the porous member defining at least a portion of a receiving chamber sized and shaped to receive the fluid port, an interior surface of the porous member being arranged to engage the fluid port when the fluid port is disposed in the receiving chamber; and a housing coupled to the porous member, the housing defining an inlet configured to be fluidly coupled to the lumen of the fluid port, an outlet configured to be fluidly coupled to the sterilization apparatus, and a fluid passageway extending between and fluidly coupling the inlet and outlet, the inlet being disposed in said at least a portion of the receiving chamber defined by the interior surface of the porous member.

E2. The port connector of statement E1, wherein at least a portion of the minute passageways of the porous member fluidly couple the receiving chamber to an exterior environment of the port connector.

E3. The port connector of statement E1, wherein the porous member is configured to form an interference fit with the fluid port.

E4. The port connector of statement E3, wherein the porous member has an inner diameter at the narrowest point of the receiving chamber, the inner diameter being equal to or less than an outer diameter of the fluid port.

E5. The port connector of statement E1, wherein the porous member has a generally tubular shape.

E6. The port connector of statement E1, wherein the housing includes a stop arranged to engage the fluid port to position the fluid port in the receiving chamber.

E7. The port connector of statement E6, wherein the stop limits the movement of the fluid port relative to the connector in an insertion direction, the insertion direction being the direction in which the fluid port moves relative to the port connector when the port connector is connected to the fluid port.

E8. The port connector of statement E6, wherein the stop is arranged to engage a distal end of the fluid port.

E9. The port connector of statement E6, wherein the stop includes an edge, the edge being arranged to engage the fluid port.

E10. The port connector of statement E9, wherein the only portion of the housing arranged to engage the fluid port is the edge of the stop.

E11. The port connector of statement E1, further comprising a guide configured to generally align the lumen of the fluid port with the inlet.

E12. The port connector of statement E11, wherein the guide is sized and shaped to be received in the lumen of the fluid port.

E13. The port connector of statement E12, wherein the guide extends through the inlet.

E14. The port connector of statement E11, wherein the guide is part of the housing, the guide extending proximally from an interior wall of the housing.

E15. The port connector of statement E1, wherein the porous member defines a proximal end of the port connector.

E16. The port connector of statement E1, wherein the porous member defines a receiving inlet at a proximal end of the receiving chamber, the receiving inlet sized and shaped to receive the fluid port.

E17. The port connector of statement E1, wherein the porous member has a proximal end portion and a distal end portion, the proximal and distal end portions being coupled to the housing.

E18. The port connector of statement E17, wherein the housing includes a cylindrical wall and a mounting ring, the distal end portion of the porous member being mounted on the cylindrical wall and the proximal end portion of the porous member being mounted on the mounting ring.

E19. The port connector of statement E18, further comprising a retaining ring, the retaining ring securing the proximal end portion of the porous member to the mounting ring.

E20. The port connector of statement E18, wherein the proximal end portion is bent around the mounting ring.

E21. The port connector of statement E18, wherein the housing includes one or more supports supporting the mounting ring.

E22. The port connector of statement E1, in combination with the fluid port, the fluid port being free of barbs on the exterior thereof.

E23. The port connector of statement E22, wherein the fluid port has a generally cylindrical exterior surface, the exterior surface being smooth.

F1. A port connector for connecting a fluid port of a device to be sterilized to a sterilization apparatus, the port connector comprising: a housing configured to couple to the fluid port, the housing defining an outlet configured to be fluidly coupled to the sterilization apparatus; a seal arranged to form a fluid tight seal with the fluid port; and a piston supported by the housing and movable relative to the housing upon the application of a pressure differential by the sterilization apparatus.

F2. The port connector of statement F1, wherein the seal is supported by the piston and moves with the piston upon the application of the pressure differential to engage the fluid port to form the fluid tight seal with the fluid port.

F3. The port connector of statement F2, wherein the seal is configured to engage the fluid port at a first location, and wherein the piston is configured to push against the fluid port upon the application of the pressure differential to move the seal to a second location on the fluid port.

It is apparent and understood that the elements, features, and/or teachings set forth in each embodiment disclosed herein are not limited to the specific embodiment(s) the elements, features, and/or teachings are described in. Accordingly, it is apparent and understood that the elements, features, and/or teachings described in one embodiment may be applied to one or more of the other embodiments disclosed herein.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

Modifications and variations of the disclosed embodiments are possible without departing from the scope of the invention defined in the appended claims. For example, where specific dimensions are given, it will be understood that they are exemplary only and other dimensions are possible. As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A port connector for connecting to a fluid port of a device to be sterilized to a sterilization apparatus, the fluid port having a distal end surface facing distally, the distal end surface defining a fluid port outlet, the fluid port defining a lumen extending proximally from the fluid port outlet, the port connector comprising: a housing configured to couple to the fluid port, the housing defining an inlet configured to be fluidly coupled to the lumen of the fluid port, an outlet configured to be fluidly coupled to the sterilization apparatus, and a fluid passageway extending between and fluidly coupling the inlet and outlet; and a porous member supported by the housing, the porous member having a porous structure defining a plurality of minute passageways, the porous member arranged relative to the housing to engage the distal end surface of the fluid port when the port connector is connected to the fluid port.

2. The port connector of claim 1, wherein the porous member is arranged relative to the housing such that at least a portion of the minute passageways fluidly couple the fluid port outlet to an exterior environment of the port connector when the port connector is connected to the fluid port.

3. The port connector of claim 1, wherein the porous member is arranged relative to the housing such that the porous member covers a portion of the fluid port outlet.

4. The port connector of claim 1, wherein the porous member includes an annular surface arranged to engage the distal end surface of the fluid port.

5. The port connector of claim 4, wherein the annular surface has an inner diameter that is less than a diameter of the fluid port outlet.

6. The port connector of claim 5, wherein the annular surface has an outer diameter that is greater than the diameter of the fluid port outlet.

7. The port connector of claim 1, wherein the housing includes an insertion portion sized and shaped to be inserting into the fluid port outlet, the insertion portion defining the inlet.

8. The port connector of claim 7, wherein the porous member is supported by the insertion portion.

9. The port connector of claim 1, wherein the housing includes a coupler configured to couple the port connector to the fluid port.

10. The port connector of claim 9, wherein the coupler comprises a first resiliently deflectable clip and a second resiliently deflectable clip, the first and second clips configured to engage the fluid port to couple the port connector to the fluid port.

11. The port connector of claim 10, wherein the first and second clips each include a retainer configured to engage the fluid port to secure the port connector to the fluid port.

12. The port connector of claim 1, further comprising a porous controlling material coating the porous member, the porous controlling material blocking a portion of the plurality of minute passageways of the porous member.

13. The port connector of claim 1, wherein the porous member has a doughnut shape.

14. The port connector of claim 1, wherein the porous member has an opening, the housing being disposed in the opening of the porous member.

15. The port connector of claim 14, wherein the housing extends through the opening of the porous member.

16. The port connector of claim 1, wherein the housing includes a stop arranged to engage the fluid port to position the port connector relative to the fluid port when the port connector is coupled to the fluid port.

17. The port connector of claim 1, wherein the housing includes a barbed tube port fitting defining the outlet and configured to couple to a tube of the sterilization apparatus.

18. The port connector of claim 1, wherein the housing is a one-piece component.

19. The port connector of claim 1, wherein the housing is multiple components secured together.

20. The port connector of claim 1, in combination with the device to be sterilized, the housing of the port connector being coupled to the fluid port of the device, the inlet of the housing being fluidly coupled to the lumen of the fluid port, the porous member of the port connector engaging the distal end surface of the fluid port.

21. The port connector of claim 20, in combination with the sterilization apparatus, the outlet of the housing of the port connector being fluidly coupled to the sterilization apparatus.

* * * * *